US011959707B2

(12) United States Patent
Lucht et al.

(10) Patent No.: US 11,959,707 B2
(45) Date of Patent: Apr. 16, 2024

(54) SYSTEMS AND METHODS FOR COOLING ULTRASOUND TRANSDUCERS AND ULTRASOUND TRANSDUCER ARRAYS

(71) Applicant: SUNNYBROOK RESEARCH INSTITUTE, Toronto (CA)

(72) Inventors: Benjamin Lucht, Toronto (CA); Samuel Gunaseelan, Toronto (CA); Kullervo Hynynen, Toronto (CA)

(73) Assignee: SUNNYBROOK RESEARCH INSTITUTE, Toronto (CA)

(*) Notice: Subject to any disclaimer, the term of this patent is extended or adjusted under 35 U.S.C. 154(b) by 562 days.

(21) Appl. No.: 17/065,078

(22) Filed: Oct. 7, 2020

(65) Prior Publication Data

US 2021/0108866 A1 Apr. 15, 2021

Related U.S. Application Data

(60) Provisional application No. 62/913,351, filed on Oct. 10, 2019.

(51) Int. Cl.
*F28F 3/06* (2006.01)
*A61B 8/00* (2006.01)
(Continued)

(52) U.S. Cl.
CPC .............. *F28F 3/06* (2013.01); *B06B 1/0696* (2013.01); *H01L 23/3672* (2013.01); *A61B 8/4483* (2013.01)

(58) Field of Classification Search
CPC ........ F28F 3/06; B06B 1/0696; B06B 1/0629; B06B 1/0662; B06B 1/0611;
(Continued)

(56) References Cited

U.S. PATENT DOCUMENTS 4,748,985 A 6/1988 Nagasaki
5,560,362 A 10/1996 Sliwa, Jr. et al.
(Continued)

FOREIGN PATENT DOCUMENTS

EP 3037179 B1 * 9/2021 ............... A61B 8/00

OTHER PUBLICATIONS

International Search report PCT/CA2020/051341 dated Feb. 18, 2021.

*Primary Examiner* — Len Tran
*Assistant Examiner* — Gustavo A Hincapie Serna
(74) *Attorney, Agent, or Firm* — HILL & SCHUMACHER

(57) ABSTRACT

Ultrasound devices and systems are disclosed in which cooling of an active acoustic element of an ultrasound transducer is achieved via an electrically conductive member that extends beyond a proximal side of the active acoustic element to contact a heat exchanger. The electrically conductive member delivers electrical driving signals to the active acoustic element while conducting heat to the heat exchanger. A region of the proximal surface of the active acoustic element that is free from contact with the electrically conductive member may also absent from contact with a liquid or a solid, thereby facilitating reflection of ultrasound energy. The heat exchanger may include an electrically insulating fluid that contacts the electrically conductive member to remove the heat conducted through the electrically conductive member. The active acoustic element may be a multilayer lateral mode element, and the electrically conductive member may form an electrode of the lateral mode element.

26 Claims, 32 Drawing Sheets

800 131 125 133 670 673 660 700 850 132 705

(51) Int. Cl.
*B06B 1/06* (2006.01)
*H01L 23/367* (2006.01)

(58) Field of Classification Search
CPC ............. H01L 23/3672; H01L 23/3677; A61B 8/4483; A61B 8/44
USPC .......................................................... 165/166
See application file for complete search history.

(56) References Cited

U.S. PATENT DOCUMENTS 5,721,463 A 2/1998 Snyder
5,938,612 A * 8/1999 Kline-Schoder ........ B06B 1/064 600/459
7,105,986 B2 * 9/2006 Wildes ................... A61B 8/546 310/334
7,314,447 B2 1/2008 Park et al.
8,004,158 B2 8/2011 Hielscher
8,162,840 B2 * 4/2012 Rosenberg ............. A61B 8/546 600/459
8,405,281 B2 * 3/2013 Kim ...................... B06B 1/0622 310/334
8,574,159 B2 * 11/2013 Kondoh ............... G01N 29/326 310/341
9,173,047 B2 * 10/2015 Lukacs .................. H10N 30/50
9,737,323 B2 8/2017 Thapliyal et al.
9,867,592 B2 * 1/2018 Davidson ............... A61B 8/546
9,899,592 B2 * 2/2018 Melz ...................... H10N 30/88
11,154,730 B2 * 10/2021 Ergün .................... A61B 8/488
11,642,105 B2 * 5/2023 Zhou ...................... A61B 8/546 600/459
2002/0073781 A1 6/2002 Hashimoto et al.
2005/0075573 A1 4/2005 Park et al.
2007/0167803 A1 7/2007 Kaminski et al.
2008/0257050 A1 10/2008 Watanabe
2009/0034370 A1 * 2/2009 Guo ..................... G10K 11/002 29/25.35
2010/0204617 A1 8/2010 Ben-Ezra
2011/0114303 A1 * 5/2011 Rhim ...................... A61B 8/00 165/185
2013/0069484 A1 3/2013 Hynynen et al.
2014/0097725 A1 * 4/2014 Peshkovsky ......... G10K 11/002 29/25.35
2015/0087988 A1 3/2015 Lee et al.
2015/0370474 A1 * 12/2015 Belaunde ............ G06F 3/04845 715/723
2017/0043189 A1 * 2/2017 Stoddard ................ G10K 11/24
2018/0055529 A1 * 3/2018 Messerly ............. H10N 30/206
2018/0056095 A1 * 3/2018 Messerly ............... H10N 30/50
2018/0066224 A1 3/2018 Lipkens et al.
2018/0078268 A1 * 3/2018 Messerly ....... A61B 17/320092
2018/0161016 A1 6/2018 Choi et al.
2018/0327256 A1 * 11/2018 Lee ....................... G01S 7/5208
2019/0142376 A1 * 5/2019 Sato ....................... A61B 8/445 600/466
2021/0165524 A1 * 6/2021 Liu ....................... B06B 1/0688

* cited by examiner

SYSTEMS AND METHODS FOR COOLING ULTRASOUND TRANSDUCERS AND ULTRASOUND TRANSDUCER ARRAYS

CROSS-REFERENCE TO RELATED APPLICATION

This application claims priority to U.S. Provisional Patent Application No. 62/913,351, titled "SYSTEMS AND METHODS FOR COOLING ULTRASOUND TRANSDUCERS AND ULTRASOUND TRANSDUCER ARRAYS" and filed on Oct. 10, 2019, the entire contents of which is incorporated herein by reference.

BACKGROUND

The present disclosure relates to ultrasound-based therapy and imaging. In some aspects, the present disclosure relates to the cooling of ultrasound transducers and ultrasound transducer array elements.

Generating ultrasound waves, particularly at high power, generates waste heat that must be dissipated to prevent damage to the transducer. Current mitigation approaches have limitations. For example, forced air cooling cannot remove heat quickly enough for use in a high-power application. Approaches that require contact of a cooling liquid with the transducer, apart from at the ultrasound emitting surface, greatly reduce the efficiency of the transducer. Similarly, attaching relatively large surface area heat sinks or exchangers to the transducer surfaces increases the mechanical loading on the device and reduces its effectiveness.

SUMMARY

Ultrasound devices and systems are disclosed in which cooling of an active acoustic element of an ultrasound transducer is achieved via an electrically conductive member that extends beyond a proximal side of the active acoustic element to contact a heat exchanger. The electrically conductive member delivers electrical driving signals to the active acoustic element while conducting heat to the heat exchanger. A region of the proximal surface of the active acoustic element that is free from contact with the electrically conductive member may also absent from contact with a liquid or a solid, thereby facilitating reflection of ultrasound energy. The heat exchanger may include an electrically insulating fluid that contacts the electrically conductive member to remove the heat conducted through the electrically conductive member. The active acoustic element may be a multilayer lateral mode element, and the electrically conductive member may form an electrode of the lateral mode element.

Accordingly, in a first aspect, there is provided an ultrasound apparatus comprising:

an active acoustic element configured to generate ultrasound energy when electrical drive signals are applied thereto, the active acoustic element having a distal surface for emitting the ultrasound energy in a distal direction and an opposing proximal surface;

an electrically conductive member contacting the active acoustic element for delivering electrical drive signals to the active acoustic element and for conducting heat from the active acoustic element, the electrically conductive member extending from the active acoustic element beyond the proximal surface such that at least a portion of the proximal surface of the active acoustic element is free from contact with the electrically conductive member, wherein the electrically conductive member is connectable to drive electronics for delivering the electrical drive signals to the active acoustic element through the electrically conductive member; and a heat exchanger spatially offset in a proximal direction from the proximal surface, the heat exchanger contacting a portion of the electrically conductive member residing beyond the proximal surface to remove heat from the active acoustic element through the electrically conductive member while delivering the electrical drive signals to the active acoustic element through the electrically conductive member.

In one example implementation of the apparatus, a region of the proximal surface that is free from contact with the electrically conductive member is also absent from contact with a liquid or a solid, thereby facilitating reflection of ultrasound energy at the portion of the proximal surface.

In one example implementation of the apparatus, a gap resides between the proximal surface and the heat exchanger, thereby facilitating reflection of ultrasound energy at the portion of the proximal surface, wherein the electrically conductive member extends across the gap to contact the heat exchanger. The gap may be an air gap. The gap may be filled with a gas other than air.

In one example implementation of the apparatus, the proximal surface comprises a signal electrode, wherein a distal end of the electrically conductive member contacts the electrode. The distal end of the electrically conductive member may contact the proximal surface within a subregion having a surface area that is less that 10% of the total surface area of the proximal surface. The distal end of the electrically conductive member may contact the proximal surface within a subregion having a surface area that is less that 5% of the total surface area of the proximal surface. The distal end of the electrically conductive member may contact the proximal surface within a subregion having a surface area that is less that 2% of the total surface area of the proximal surface.

A cross-sectional area of the electrically conductive member, within the portion of the electrically conductive member that contacts the heat exchanger, may be greater than a cross-sectional area of the electrically conductive member at the distal end of the electrically conductive member. A cross-sectional area of the electrically conductive member, within the portion of the electrically conductive member that contacts the heat exchanger, may be smaller than a cross-sectional area of the electrically conductive member at the distal end of the electrically conductive member. A cross-sectional area of the electrically conductive member, within the portion of the electrically conductive member that contacts the heat exchanger, may be variable and is greater and/or smaller than a cross-sectional area of the electrically conductive member at the distal end of the electrically conductive member. A cross-sectional area of the electrically conductive member, within the portion of the electrically conductive member that contacts the heat exchanger, may be uneven, non-symmetric, rough or has extensions or other structures, shapes, or surface patterns or micro-structures to enhance heat transfer.

In one example implementation of the apparatus, a portion of the proximal surface that is free from contact with the electrically conductive member contacts a material having an acoustic impedance selected such that at least 50% of backward-propagating ultrasound energy is reflected at the portion of the proximal surface.

In one example implementation of the apparatus, a portion of the proximal surface that is free from contact with the electrically conductive member contacts a material having an acoustic impedance selected to match an acoustic impedance of the active acoustic element so that backward-propagating ultrasound energy is supressed at the portion of the proximal surface.

In one example implementation of the apparatus, a portion of the proximal surface that is free from contact with the electrically conductive member contacts a material having an acoustic impedance selected such that less than 10% of backward-propagating ultrasound energy is reflected at the portion of the proximal surface. The electrically conductive member may extend from the proximal surface and passes through the material prior to contacting the heat exchanger. The material may contact the heat exchanger for facilitating removal of heat conducted through the material. The material may be acoustically attenuating.

In one example implementation of the apparatus, a distal region of the electrically conductive member contacts an electrode of the active acoustic element.

In one example implementation of the apparatus, a distal region of the electrically conductive member forms an electrode of the active acoustic element.

In one example implementation of the apparatus, the heat exchanger comprises an electrically insulating fluid, the electrically insulating fluid contacting the portion of the electrically conductive member to remove the heat conducted through the electrically conductive member without contacting the active acoustic element.

The portion of the electrically conductive member contacting the electrically insulating fluid may comprise a cylindrical segment. The portion of the electrically conductive member contacting the electrically insulating fluid may comprise a planar fin. The portion of the electrically conductive member contacting the electrically insulating fluid may comprise an elongate segment extending across the heat exchanger, the elongate segment having one or more lateral members extending laterally therefrom.

The apparatus may further comprise a pump configured to flow the electrically insulating fluid through the heat exchanger. The heat exchanger may be a first heat exchanger, and the ultrasound apparatus may further comprising a second heat exchanger located on a distal side of the distal surface, the second heat exchanger being in thermal communication with the active acoustic element, such that heat generated within the active acoustic element is removed on a proximal side of the active acoustic element by the first heat exchanger and is removed on a distal side of the active acoustic element by the second heat exchanger.

The heat exchanger may comprise a thermo-electric cooler.

In one example implementation of the apparatus, the active acoustic element is a lateral model active acoustic element comprising a plurality of piezoelectric layers having electrodes provided therebetween for exciting lateral mode ultrasound emission in the distal direction. A distal region of the electrically conductive member may form an electrode of the lateral model active acoustic element.

In one example implementation, the apparatus may further comprise a printed circuit board residing on a proximal side of the heat exchanger, wherein the electrically conductive member extends beyond the heat exchanger and is connected to the printed circuit board for delivering the electrical drive signals.

In one example implementation of the apparatus, the electrically conductive member may comprise a first segment contacting the active acoustic element and a second segment contacting the heat exchanger, wherein the first segment is detachably connected to the second segment to facilitate modular assembly of the ultrasound apparatus. A cross-sectional diameter of the first segment may be less than a cross-sectional diameter of the second segment. One of the first segment and the second segment may comprise a socket for receiving the other of the first segment and the second segment. The apparatus may further comprise a housing configured to support the active acoustic element and the first segment of the electrically conductive member.

In one example implementation of the apparatus, the electrically conductive member is a first electrically conductive member, the ultrasound apparatus further comprising a second electrically conductive member; the second electrically conductive member extending from the active acoustic element beyond the proximal surface such that at least a portion of the proximal surface of the active acoustic element is free from contact with the second electrically conductive member, wherein the second electrically conductive member is connectable to drive electronics for delivering the electrical drive signals to the active acoustic element through the second electrically conductive member. The first electrically conductive member and the second electrically conductive member may contact different regions of the proximal surface. The second electrically conductive member may contact a ground electrode of the active acoustic element.

In one example implementation of the apparatus, the active acoustic element is a first active acoustic element and the electrically conductive member is a first electrically conductive member, the ultrasound apparatus further comprising one or more additional acoustic active elements, each additional acoustic active element having a respective additional electrically conductive member extending therefrom beyond a respective proximal surface thereof such that a portion of each additional electrically conductive member contacts the heat exchanger, the first active acoustic element and the additional acoustic active elements defining a set of active acoustic elements, and the first electrically conductive member and the additional electrically conductive member defining a set of electrically conductive members, wherein the set of active acoustic elements and the set of electrically conductive members are spatially arranged to form an ultrasound array. The heat exchanger may comprise an electrically insulating fluid, the electrically insulating fluid contacting the portion of each electrically conductive member to remove the heat conducted through the electrically conductive member. The apparatus may further comprise an insulating spacer residing within the heat exchanger, the insulating spacer configured to prevent contact between the electrically conductive members. The apparatus may further comprise a housing configured to support the set of active acoustic elements.

Each electrically conductive member of the set of electrically conductive members may comprise a first segment contacting a respective active acoustic element and a second segment contacting the heat exchanger, wherein each first segment is supported by the housing; wherein the housing, the set of active acoustic elements and the set of first segments form an array module; and wherein the set of second segments form a cooling array supported by the heat exchanger; and wherein each first segment is detachably connected to a respective second segment, such that the array module is detachable from the cooling array to facilitate modular assembly of the ultrasound apparatus with the heat exchanger.

A cross-sectional diameter of the first segment may be less than a cross-sectional diameter of the second segment. One of the first segment and the second segment may comprise a socket for receiving the other of the first segment and the second segment. The array module may be a first array module and the cooling array may be a first cooling array, and the ultrasound apparatus may further comprise one or more additional array modules and one or more respective cooling arrays. Each array module may be connected, through a respective cooling array, to a respective circuit board, and wherein each circuit board is connected to dedicated per-module drive electronics.

In another aspect, there is provided an ultrasound apparatus comprising:

- an active acoustic element configured to generate ultrasound energy when electrical drive signals are applied thereto, the active acoustic element having a distal surface for emitting the ultrasound energy in a distal direction and an opposing proximal surface;
- an electrically conductive member contacting the active acoustic element for delivering electrical drive signals to the active acoustic element and for conducting heat from the active acoustic element, the electrically conductive member extending from the active acoustic element beyond the proximal surface such that at least a portion of the proximal surface of the active acoustic element is free from contact with the electrically conductive member;
- a circuit board spatially offset in a proximal direction from the proximal surface, wherein a proximal end of the electrically conductive member is in electrical contact with the circuit board for delivering the electrical drive signals to the active acoustic element; and
- a heat exchanger in thermal contact with the circuit board for removing heat conducted through the electrically conductive member and through the circuit board.

In another aspect, there is provided a lateral mode ultrasound transducer comprising:

- a piezoelectric stack comprising two or more piezoelectric layers, wherein the two or more piezoelectric layers are stacked along a first direction;
- a plurality of electrodes, the plurality of electrodes comprising:
  - a pair of outer electrodes formed on respective outer surfaces of the piezoelectric stack, and
  - a set of internal electrodes, each internal electrode residing between adjacent piezoelectric layers of the piezoelectric stack;
- a first common electrode in electrical communication with a first subset of the plurality of electrodes; and
- a second common electrode in electrical communication with a second subset of the plurality of electrodes;
- the first subset of the plurality of electrodes and the second subset of the plurality of electrodes being selected such that when a driving signal is applied between the first common electrode and the second common electrode at a frequency associate with a lateral mode coupled resonance of the piezoelectric stack:
  - the driving signal is applied in opposing directions among neighbouring piezoelectric layers of the piezoelectric stack; and
  - lateral mode coupling causes the piezoelectric stack to be mechanically responsive along a second direction that is perpendicular to the first direction, thereby producing ultrasound emission along the second direction;
- wherein the first common electrode resides, at least in part, on a distal surface of the piezoelectric stack, the distal surface being perpendicular to the second direction, and wherein the second common electrode resides, at least in part, on a proximal surface opposing the distal surface;
- wherein each internal electrode of the second subset of electrodes is electrically isolated from the first common electrode by a respective electrically insulating channel residing proximal to the distal surface and extending, from the distal surface, in a proximal direction; and
- wherein each internal electrode of the first subset of electrodes is electrically isolated from the second common electrode by a respective electrically insulating channel residing proximal to the proximal surface and extending, from the proximal surface, in a distal direction.

In another aspect, there is provided an ultrasound apparatus comprising:

- a housing;
- an array of active acoustic elements supported by the housing, each active acoustic element having a respective distal ultrasound emitting surface and a respective proximal surface;
- a first array of first electrically conductive members supported such that each active acoustic element is in electrical communication with a respective first electrically conductive member for providing electrical driving signals thereto, and wherein each first electrically conductive member extends, in a proximal direction, beyond a respective proximal surface of a respective active acoustic element connected thereto;
- a heat exchanger; and
- a second array of second electrically conductive members supported by and thermally contacting the heat exchanger;
- wherein the first array of first electrically conductive members are connectable to the second array of second electrically conductive members for cooling the array of active acoustic elements with the heat exchanger via the conduction of heat from the array of active acoustic elements to the heat exchanger through the first array of electrical conductive members and the second array of electrically conductive members; and
- wherein the second array of second electrically conductive members extend through the heat exchanger and are connectable to drive electronics for delivering the electrical driving signals to the array of active acoustic elements while simultaneously cooling the array of active acoustic elements.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
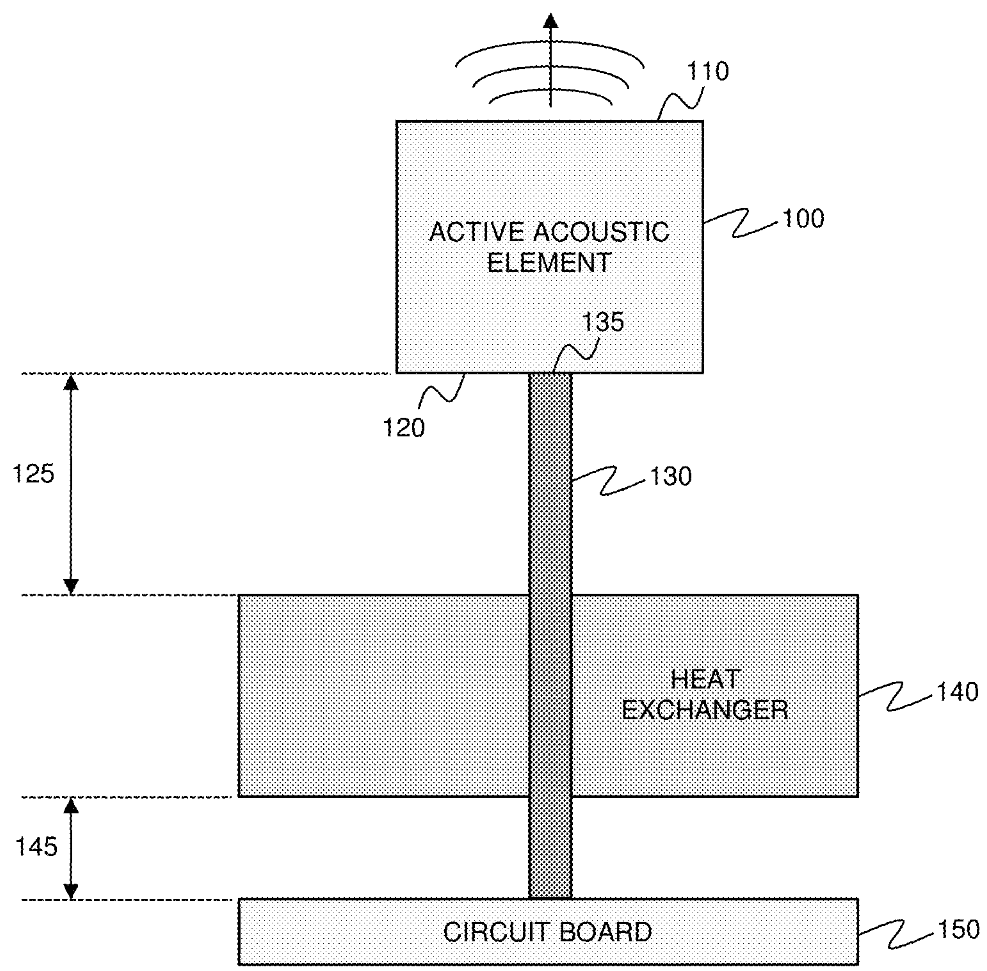
FIG. 1A shows a cross-sectional view of an example proximally cooled ultrasound transducer apparatus in which an electrically conductive member is in contact with an active acoustic element of an ultrasound transducer and also in contact with a proximal heat exchanger for delivering electrical driving signals to the active acoustic element of an ultrasound transducer and for removing heat from the active acoustic element.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms “comprises” and “comprising” are to be construed as being inclusive and open ended, and not exclusive. Specifically, when used in the specification and claims, the terms “comprises” and “comprising” and variations thereof mean the specified features, steps or components are included. These terms are not to be interpreted to exclude the presence of other features, steps or components.

As used herein, the term “exemplary” means “serving as an example, instance, or illustration,” and should not be construed as preferred or advantageous over other configurations disclosed herein.

As used herein, the terms “about” and “approximately” are meant to cover variations that may exist in the upper and lower limits of the ranges of values, such as variations in properties, parameters, and dimensions. Unless otherwise specified, the terms “about” and “approximately” mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term “on the order of”, when used in conjunction with a quantity or parameter, refers to a range spanning approximately one tenth to ten times the stated quantity or parameter.

The present inventors sought to overcome the aforementioned limitations of conventional ultrasound transducer cooling methods. Instead of employing conventional approaches in which an ultrasound transducer is cooled via direct contact with a cooling fluid, which can impede the transducer performance due to acoustic coupling of the cooling fluid with the ultrasound transducer, the present inventors sought a conductive cooling solution that would achieve efficient cooling while avoiding unnecessary or undue fluidic or mechanical contact with the ultrasound transducer. The present inventors also sought a compact solution that would be adaptable to individual ultrasound transducers and also to ultrasound array elements.

The present inventors realized that an ultrasound transducer could be cooled on its proximal side while minimally impacting its acoustic performance by employing an electrical conductor to deliver electrical drive signals to the ultrasound transducer and to also serve as a path for heat extraction via thermal conduction. Such an approach was found by the inventors to be beneficial in reducing or minimizing mechanical contact with the ultrasound transducer and avoiding fluidic contact with the ultrasound transducer.

An example of such an embodiment is shown in FIG. 1A, which shows an ultrasound apparatus that includes an active acoustic element 100 having a distal surface 110 for emitting ultrasound energy and an opposing proximal surface 120. The figure schematically illustrates the proximal cooling of the active acoustic element 100 via a heat exchanger 140, where the heat exchanger 140 is in thermal contact with the active acoustic element 100 via an electrically conductive member 130 that also delivers electrical driving signals to the active acoustic element 100.

As shown in FIG. 1A, the electrically conductive member 130 contacts the active acoustic element 100 to deliver the electrical drive signals to the active acoustic element 100 for the generation of ultrasound energy, and also contacts the heat exchanger 140 to remove heat generated within the active acoustic element 100. In some example embodiments in which the ultrasound transducer is employed for detection, the electrically conductive member 130 may also be employed for the delivery of detected signals to detection circuitry (e.g. for the generation of an ultrasound image).

The electrically conductive member 130 extends from the active acoustic element 100, beyond the proximal surface 120 of the active acoustic element 100, to contact the heat exchanger 140, which is spatially offset (in the proximal direction) from the proximal surface 120. Heat generated within the active acoustic element 100 is thus thermally conducted though the electrically conductive member 130 to the heat exchanger 140 while electrical drive signals are delivered, through the electrically conductive member 130, to the active acoustic element 100.

In the example embodiment illustrated in FIG. 1A, the electrical drive signals are delivered through the electrically conductive member 130 via contact of the electrically conductive member 130 with the circuit board 150 (e.g. a flexible printed circuit board). The circuit board may include drive electronics or may provide a conducive path to drive electronics that are remotely located. Alternatively, the electrically conductive member 130 may contact, at a proximal end or region thereof, a wire, cable, a ball-grid array of solder balls, or other electrical connector or conduit to facilitate the delivery of the electrical driving signals.

The electrically conductive member 130 has a sufficient electrical conductivity to facilitate the delivery of electrical drive signals to the active acoustic element 100. Non-limiting examples of electrically conductive materials for forming the electrically conductive member that is also thermally conductive include metals, alloys, doped semiconductors, and non-metallic electrical conductors such as graphite and conductive polymers. In some example embodiments, the electrically conductive member is formed from a material having an electrical conductivity of at least $10^5$ S/m and a thermal conductivity of at least 1 W/m·K.

Figure 1B:
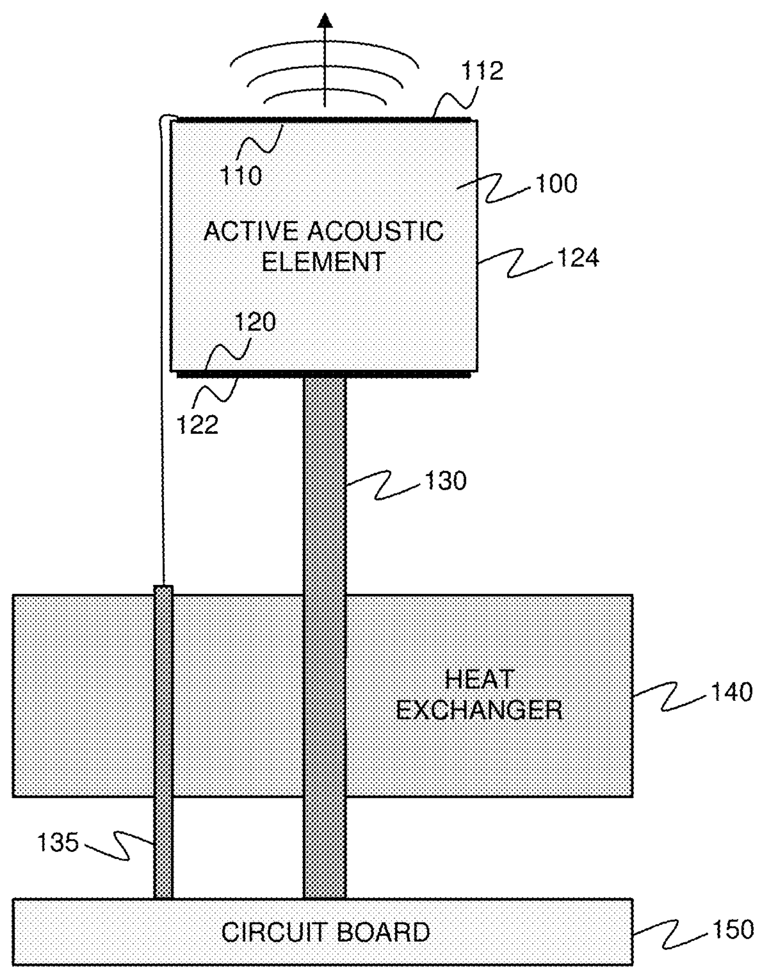
FIG. 1B shows a cross-sectional view of an example proximally-cooled ultrasound transducer apparatus, illustrating an example configuration in which a ground connection is also made through the heat exchanger.

In some example implementations, the electrically conductive member 130 may contact an electrode of the active acoustic element 100 (such an electrode is not shown in FIG. 1A), while in other example implementations, the electrically conductive member 130 may itself form an electrode of the active acoustic element 100. FIG. 1B illustrates an example configuration in which the electrically conductive member 130 contacts an electrode 122 residing on a surface of the active acoustic element. While FIG. 1B shows the electrically conductive member 130 contacting an electrode 122 residing on the proximal surface 120, in alternative example implementations, the electrically conductive member 130 may contact an electrode residing on a lateral surface of the active acoustic element, such as an electrode formed on surface 124.

Although not shown in FIG. 1A, a separate conductive path may be employed to facilitate a connection of an electrode of the active acoustic element 110 to ground. An example ground connection is shown in FIG. 1B, in which connection is made with a ground electrode 112 residing on the distal surface 110 of the active acoustic element 100. In the example implementation shown in FIG. 1B, the ground electrode 112 may be brought into electrical communication with an additional electrically conductive member 135 that also extends through and contacts the heat exchanger 140. In other example implementations, the ground connection may be made without contact with the heat exchanger 140.

Figure 1C:
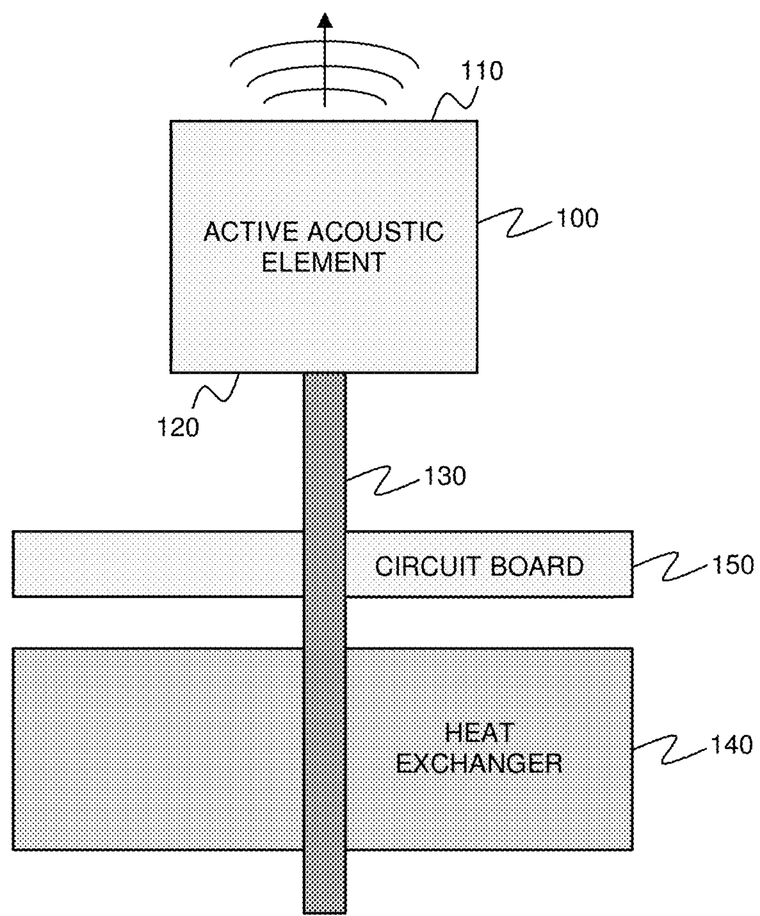
FIG. 1C shows a cross-sectional view of an example proximally-cooled ultrasound transducer apparatus, illustrating an example configuration in which a circuit board resides between the proximal surface of the active acoustic element and the heat exchanger.

Although the preceding embodiments show and describe the circuit board (or cable/connector) being located on a proximal side of the heat exchanger, such that the heat exchanger resides between the circuit board and the proximal surface of the active acoustic element, the circuit board (or cable/connector) may alternatively be located between the proximal surface of the active acoustic element and the heat exchanger, such that the electrically conductive member passes through the circuit board (or cable/connector), contacting a conductive path of the circuit board (or cable/connector) for the delivery of the electrical drive signals, and further extends, in a proximal direction, to contact the heat exchanger. According to such an alternative example embodiment, which is illustrated in FIG. 1C, some of the heat conducted through the distal portion of the electrically conductive member 130 that resides between the circuit board 150 and the proximal surface 120 of the active acoustic element 100 may be removed by the thermal mass of the circuit board (or cable/connector), with a remainder of the heat being removed by the heat exchanger 140. Alternatively, in cases in which the circuit board includes active electrical components that also generate heat, the heat exchanger may remove heat generated by both the active acoustic element 100 and the circuit board 150.

Figure 1D:
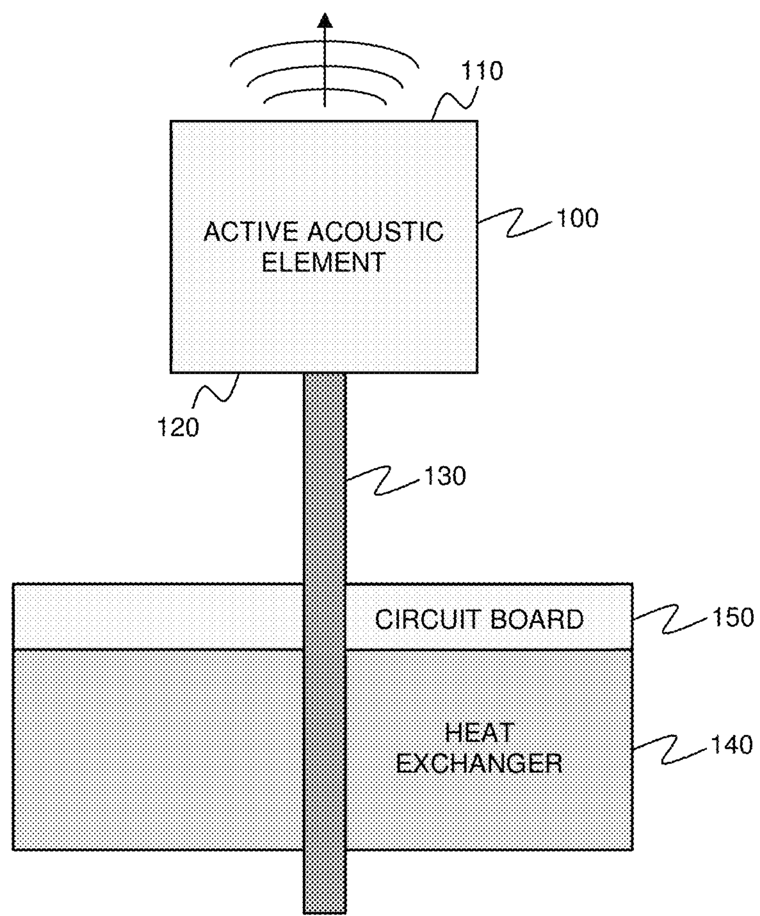
FIGS. 1D and 1E show example embodiments in which the electrically conductive member is in electrical and thermal contact with the circuit board, and where the circuit board is in thermal contact with the heat exchanger.

While the example embodiment illustrated in FIG. 10 shows a gap residing between the circuit board 150 and the heat exchanger 140, it will be understood that the circuit board 150 may be in direct thermal contact with the heat exchanger 140. For example, as shown in FIG. 1D, the electrically conductive member 130 may pass though the circuit board 150 prior to contacting the heat exchanger 140. Such an example embodiment may be particularly useful when the circuit board 150 includes active electrical components that generate heat, in which case the heat exchanger 140 can be employed to remove heat from the both the circuit board 150 and the active acoustic element 100.

Figure 1E:
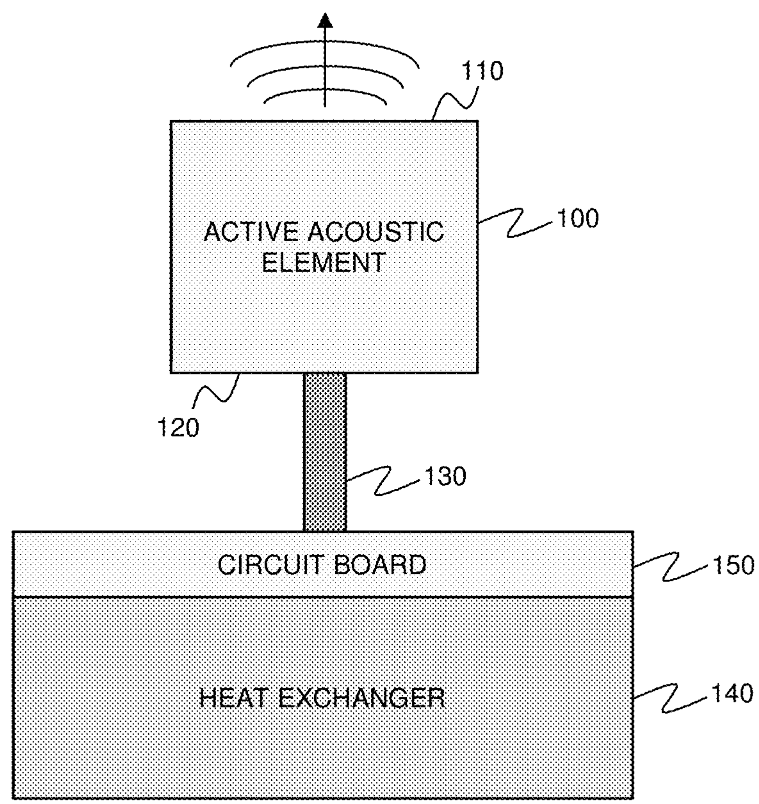

FIG. 1E illustrates an alternative example embodiment in which a proximal end of the electrically conductive member 130 contacts the circuit board 150, such that the electrically conductive member 130 is in indirect thermal contact with the heat exchanger 150 via the intermediate circuit board 150. In such a case, the heat generated within the active acoustic element 100 is conducted through the circuit board 150 and subsequently extracted by the heat exchanger 140. In various example embodiments illustrated herein, the electrically conductive member 130 contacts the active acoustic element 100 such that at least a portion of the proximal surface 120 of the active acoustic element 100 is free from contact with the electrically conductive member 130. Such limited contact or absence of contact of the proximal surface with the electrically conductive member 130 reduces or avoids, respectively, the generation of reflected ultrasound waves from the backwardly propagating ultrasound waves generated within the active acoustic element 100, and also reduces the perturbation of the mechanical response of the active acoustic element 100 to electrical drive signals that is caused by the presence of the electrically conductive member 130.

Although not shown in FIG. 1A, the ultrasound transducer may include one or more layers in addition to the acoustically active element 100, such as, but not limited to, one or more impedance matching layers, an acoustic lens, a waterproofing and/or electrically insulating distal membrane, one or more electrodes, and a backing layer.

In the example embodiment shown in FIG. 1A, a distal end of the electrically conductive member 130 only contacts a subregion of the proximal surface 120 of the active acoustic element 100, such that a substantial fraction of the surface area of the proximal surface 120 is free from contact with the electrically conductive member 130. According to such example embodiments, the distal end of the electrically conductive member 130 may contact a subregion of the proximal surface 120 of the active acoustic element 100 that is a fraction of the total surface area of the proximal surface 120, where the fraction may be less than 50%, less than 40%, less than 30%, less than 20%, less than 10%, less than 5%, less than 2%, or less than 1%. In some example embodiments, the distal end of the electrically conductive member has a surface area that is less than 1 $mm^2$, less than 0.5 $mm^2$, less than 0.2 $mm^2$, less than 0.01 $mm^2$, less than 0.05 $mm^2$, less than 0.02 $mm^2$, or less than 0.01 $mm^2$.

It will be understood that the ability of the electrically conductive member 130 to remove heat from the active acoustic element is dependent on a number of factors, such as, but not limited to, the thermal conductivity of the electrically conductive member, the contact area between the electrically conductive member and the proximal surface 120 of the active acoustic element 100, the contact area between the electrically conductive member and the heat exchanger 140, and thermal properties of the heat exchanger. These parameters may be varied by the skilled artisan in order to identify suitable values for a given application (e.g. in order to achieve a sufficient amount of heat extraction or in order to achieve a prescribed operating temperature of the active acoustic element 100).

In several example embodiments disclosed herein, at least a portion of the region of the proximal surface 120 that is free from contact from the electrically conductive member 130 is also absent from contact with a liquid or a solid. Such a configuration facilitates reflection of ultrasound energy within the region of the surface that is absent from contact, which may increase the output acoustic power and provide an improvement in applications such as therapeutic ultrasound procedures. Such an example embodiment is shown in FIG. 1A, in which a gap 125 resides between the proximal surface 120 of the active acoustic element 100 and the heat exchanger 140, the gap being spanned by a portion of the electrically conductive member 130. In some example embodiments, a gas such as air, or a gas other than air, may reside within the gap, or the gap may be a vacuum or a gas (e.g. air) at sub-atmospheric pressure. The gas may be actively flowed across to gap to remove heat from the portion of the electrically conductive member spanning the gap and from the top surface of the heat exchanger (e.g. forced-fluid cooling).

The gap 125 need only be sufficiently large to establish a hard acoustic reflection at the proximal surface 120. A suitable gap size may be determined experimentally, for example, by constructing or simulating a series of transducer apparatus with different gap sizes and determining a minimum gap size that facilitates a sufficiently large reflection (or a sufficiently large acoustic output power from the ultrasound transducer). In one example embodiment, the gap is at least 1 mm.

Although an additional gap 145 is also shown between the heat exchanger 140 and the circuit board 150, it will be understood that in other example implementations the heat exchanger 140 may directly contact the circuit board 150.

Figure 2:
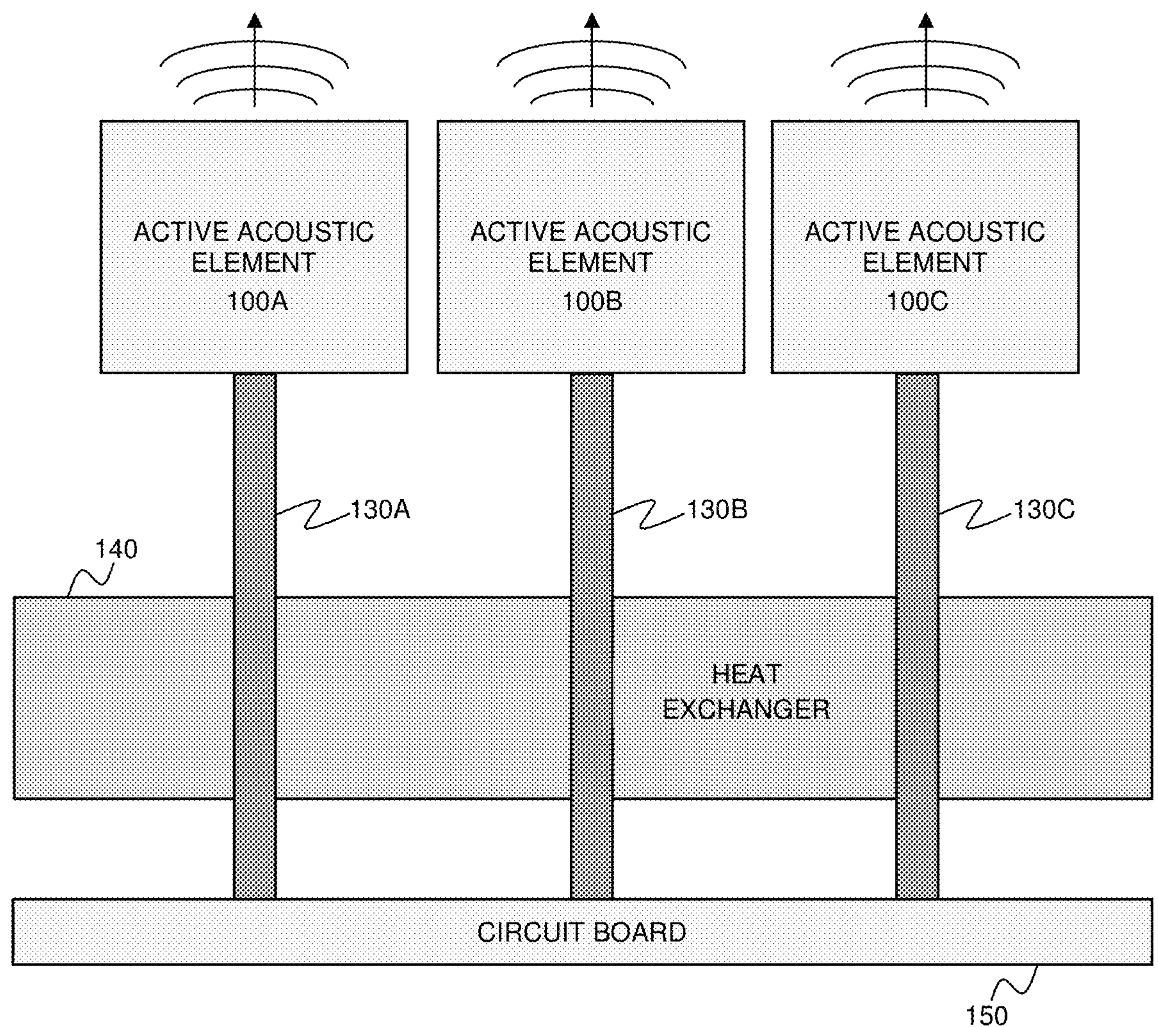
FIG. 2 schematically illustrates an example embodiment in which an array of ultrasound transducer array elements is proximally-cooled via per-element electrically conductive members that contact a common heat exchanger.

Although FIGS. 1A and 1B illustrate example embodiments involving a single ultrasound transducer (showing a single active acoustic element 100), the proximally-cooled transducer apparatus may include a plurality of active acoustic elements. The plurality of active acoustic elements may be arranged in an ultrasound array, such as a phased array of active acoustic elements. An example of such an embodiment is illustrated in FIG. 2, which shows a plurality of active acoustic elements 100A-100C arranged in an array, with each active acoustic element being proximally-cooled via respective per-element electrically conductive members 130A-130C that contact a common heat exchanger 140. The figure shows an example implementation in which the per-element electrically conductive members 130A-130C extend, proximally, beyond the common heat exchanger, to contact a common circuit board 150 (or common connector/cable), although in alternative implementations the electrically conductive members 130A-130C can contact separate wires, cables, or connectors. The active acoustic elements may be arranged with a center-to-center spacing of one half of their operating wavelength or less.

Although the figure illustrates an example case involving a linear array of ultrasound transducers, it will be understood that the array may alternatively be a two-dimensional array (such as a planar two-dimensional ultrasound transducer array or curved two-dimensional ultrasound transducer array). As can be seen in the FIG. 2, the present example embodiment that employs per-element electrically conductive members 130A-130C which extend, from their respective active acoustic elements 100A-100C, beyond the respective proximal surfaces in the proximal direction to contact the common heat exchanger 140, enables a compact configuration for conductive cooling of the active acoustic elements 100A-100C while avoiding unnecessary mechanical contact with the active acoustic elements, thus reducing the mechanical loading and the associated perturbation to mechanical response of the elements.

It will be understood that the heat exchanger 140 may be any device that is capable of removing heat from the electrically conductive member and transferring the heat to a fluid. An example of heat exchanger is a heat sink that is in thermal communication with a fluid such as air or a coolant that flows relative to the heat sink. In such a case, the region of the heat sink that is contacted by the electrically conductive member may be electrically insulating (preventing the flow of current) while permitting heat conduction. The heat exchanger may include an active cooling device such as a thermo-electric cooler.

Figure 3A:
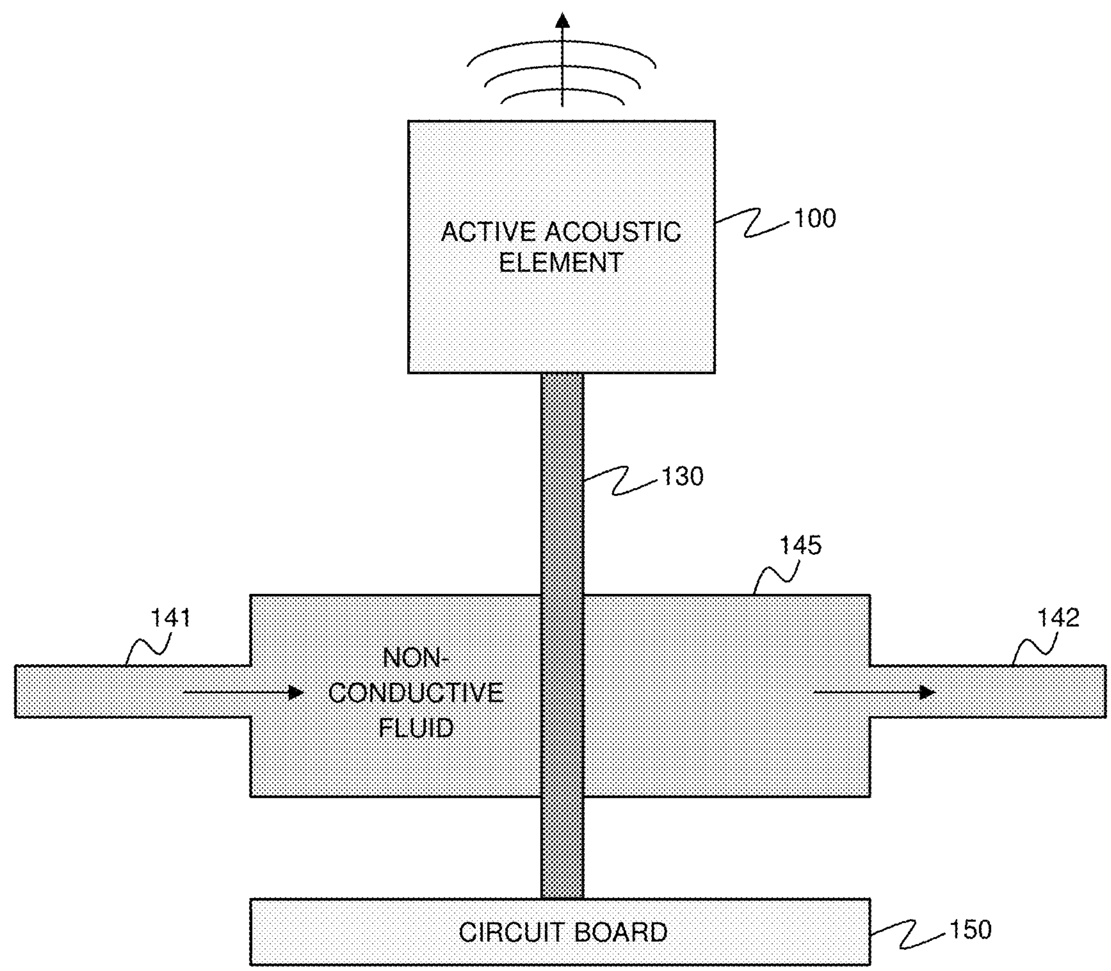
FIG. 3A shows a cross-sectional view of an example proximally-cooled ultrasound transducer apparatus, illustrating an example configuration in which the heat exchanger employs an electrically insulating fluid contacting the electrically-conductive member to remove heat therefrom.

FIG. 3A illustrates an example embodiment of a heat exchanger in which an electrically insulating (yet thermally conductive) fluid that is introduced through an inlet 141 of a heat exchanger housing 145 thermally contacts the electrically conductive member 130 to remove heat therefrom. The electrically insulating fluid flows through an outlet 142 in the heat exchanger housing 145, removing the heat. After flowing through the outlet 142, the electrically insulating fluid is externally cooled (e.g. via an external heat exchanger that transfers the heat to another fluid, or via dissipation and/or contact with a remote fluid reservoir) and is recirculated by a pump (not shown). In some example embodiments, the temperature of the electrically insulating fluid may be externally controlled (e.g. via direct cooling or an external heat exchanger with feedback from a temperature sensor). The electrically conductive member 130 may contact an o-ring, upon entry or exit from the heat exchanger housing to prevent leakage around the interface between the heat exchanger housing 145 and the electrically conductive member 130. Alternatively such an interface may be sealed with an adhesive, such as epoxy.

Examples of electrically insulating fluids include air or other gases and non-electrically conductive liquids. Non-limiting examples of electrically insulating liquids include oil, deionized water, or specially-engineered heat transfer fluid, such as 3M's Novec series. In the example case of a heat exchanger that employs an electrically insulating liquid, the electrically conductive member may be in both direct electrical and thermal contact with the electrically insulating fluid within the heat exchanger housing.

Figure 3B:
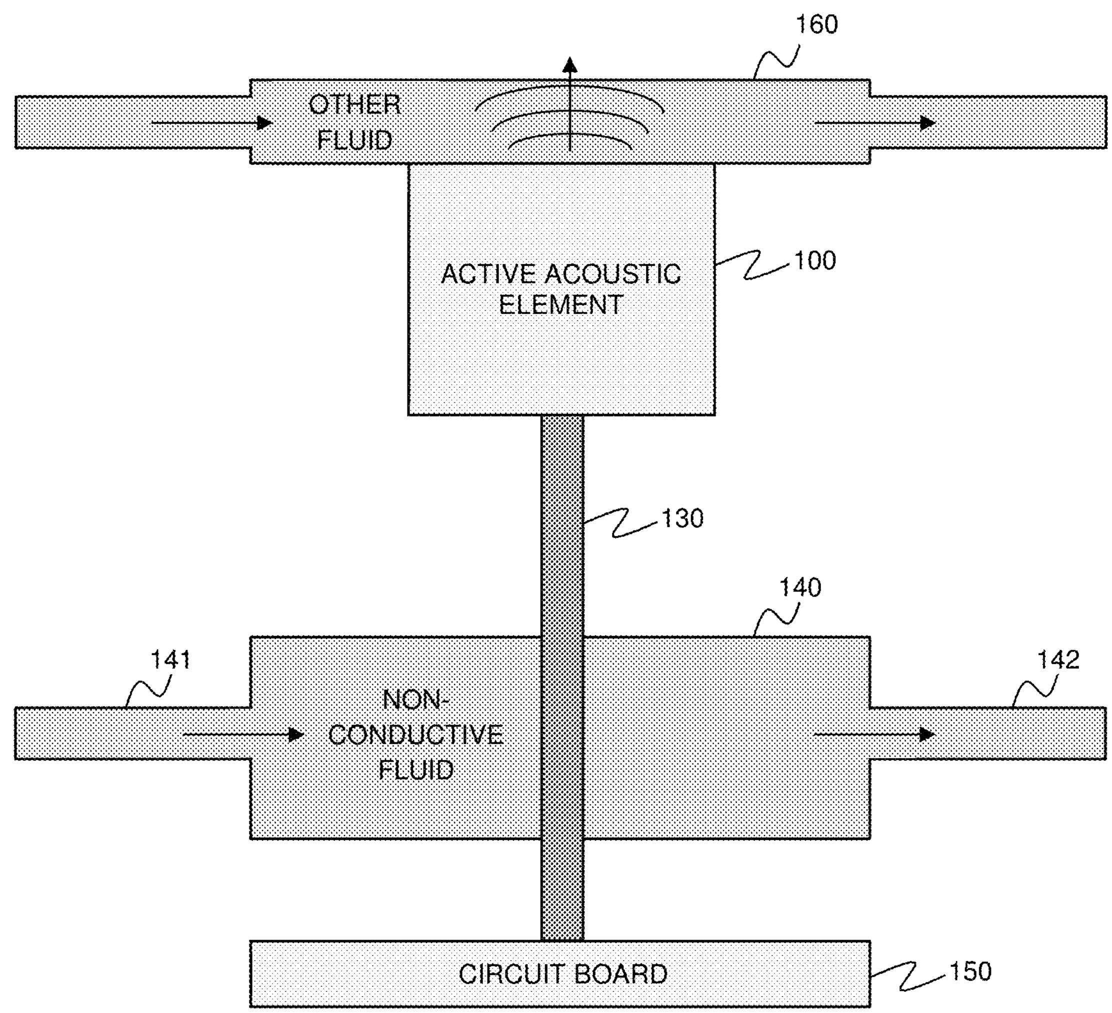
FIG. 3B shows a cross-sectional view of an example proximally-cooled ultrasound transducer apparatus in which a dual heat exchanger configuration is illustrated, with separate fluid-based heat exchanger loops employed on the proximal and distal surfaces of the active acoustic element of the ultrasound transducer for efficient heat removal.

In some example embodiments, an additional active forced-flow fluidic heat exchanger 160 may contact the ultrasound transducer on the distal side of the active acoustic element 100, as shown in FIG. 3B. The fluid flowing in this additional heat exchanger may be different than the fluid flowing in the proximal heat exchanger 140, since the distal heat exchanger 160 need not contact any conductive portions of the ultrasound element, and instead may simply thermally contact a distal surface of the ultrasound transducer (e.g. the distal surface of the active acoustic element 100 or the distal surface of an index matching layer or acoustic lens). This distal fluid may also be used as an acoustic coupling medium between the active acoustic element 100 and the target region.

Figure 4:
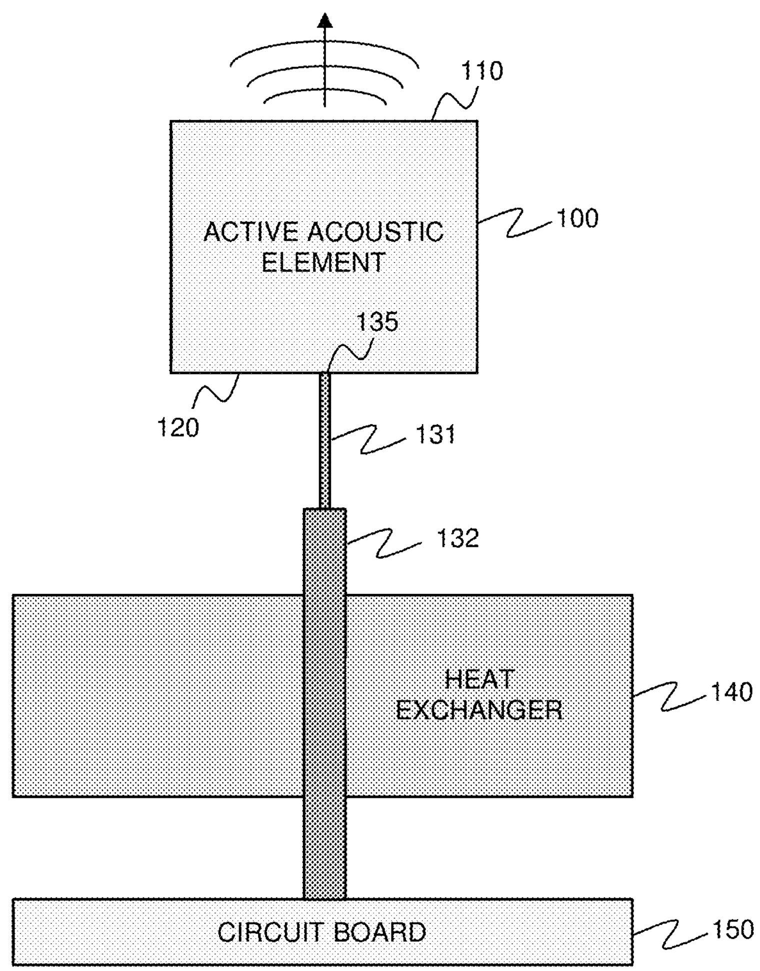
FIG. 4 shows a cross-sectional view of an example proximally-cooled ultrasound transducer apparatus in which the electrically conductive member extends beyond the proximal surface of the active acoustic element of the ultrasound transducer and varies in cross-sectional area, illustrating an example case in which the cross-sectional area at the location of contact with the proximal surface of the active acoustic element is less than the cross-sectional area within the region of contact with the heat exchanger.

Although the example embodiments shown in the preceding figures illustrate an example case in which the electrically conductive member has a constant cross-sectional diameter along its length, it will be understood that the electrically conductive member may have a varying diameter and/or shape (e.g. along its elongate direction). FIG. 4 illustrates an example embodiment in which the electrically conductive member varies in cross-sectional diameter, illustrating an example case in which the electrically conductive member includes a first elongate portion 131 and a second elongate portion 132 having different cross-sectional diameters. In particular, the figure shows an example embodiment in which the cross-sectional diameter of the electrically conductive member at the location of contact with the proximal surface of the active acoustic element is less than the cross-sectional diameter within the region of contact with the heat exchanger. Such an example embodiment may be beneficial in reducing the contact area between the electrically conductive member and the proximal surface 120 of the active acoustic element 130 while providing a larger surface area for heat conduction in the vicinity of the heat exchanger. In another example embodiment, the cross-sectional diameter of the electrically conductive member at the location of contact with the proximal surface of the active acoustic element may be greater than the cross-sectional diameter within the region of contact with the heat exchanger. In another example embodiment, the cross-sectional diameter of the electrically conductive member at the location of contact with the proximal surface of the active acoustic element may be less than the cross-sectional diameter within the region of contact with the heat exchanger.

In some example embodiments, the first and second portions of the electrically conductive member may be formed from different materials. For example, the distal portion 131 of the electrically conductive member, which has a smaller cross-sectional area, may be formed from a material having a higher thermal conductivity than that of the proximal portion 132.

Figure 5A:
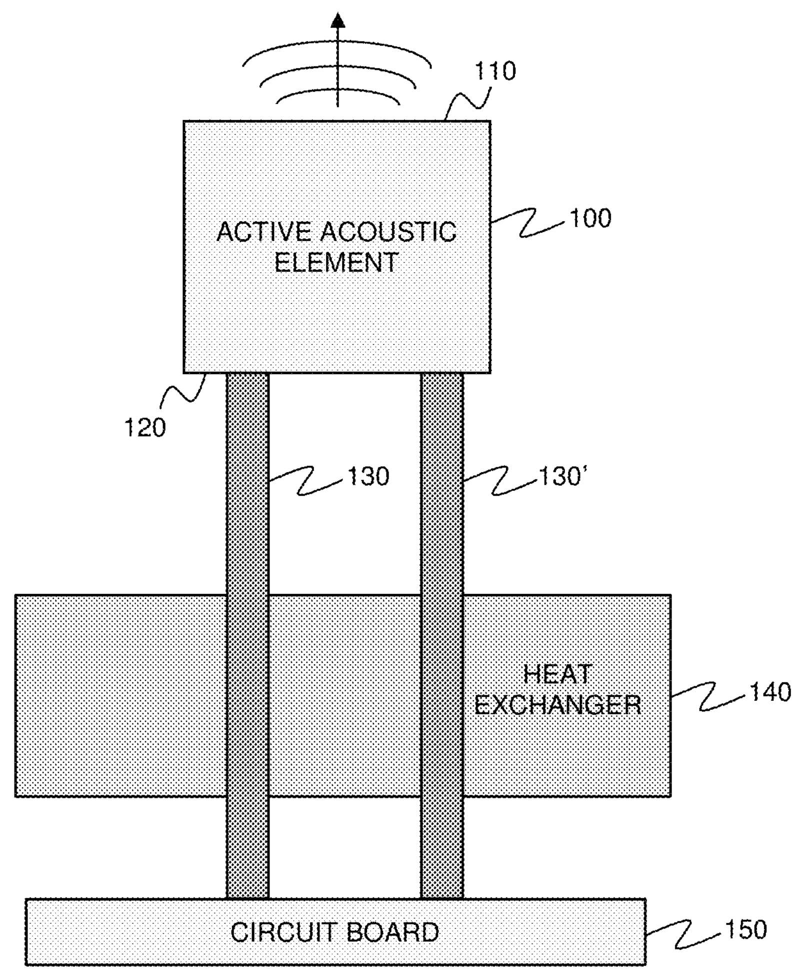
FIG. 5A shows a cross-sectional view of an example proximally-cooled ultrasound transducer apparatus in which multiple electrically conductive members extend beyond the proximal surface of the active acoustic element to contact the heat exchanger.
Figure 5B:
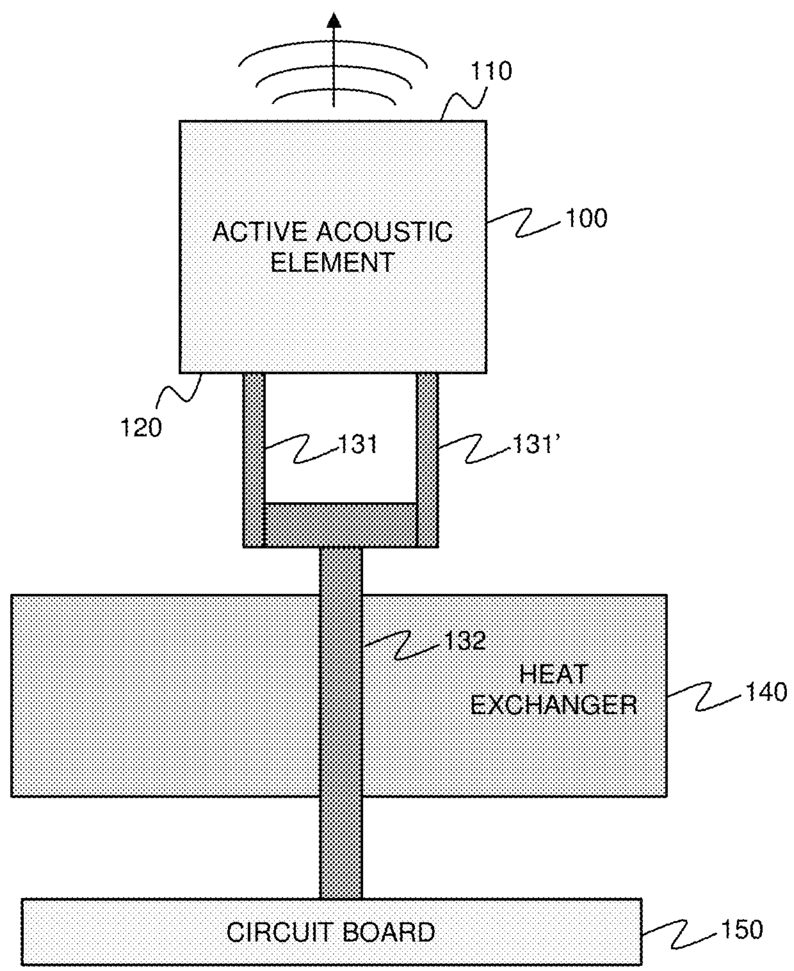
FIG. 5B shows a cross-sectional view of an example proximally-cooled ultrasound transducer apparatus in which multiple electrically conductive members extend beyond the proximal surface and merge into a common proximal electrically conductive segment that contacts the heat exchanger.

In some example embodiments, two or more electrically conductive members may contact the active acoustic element. This example embodiment is illustrated in FIG. 5A, which shows an example proximally-cooled ultrasound transducer apparatus in which two electrically conductive members 130 and 130' extend beyond the proximal surface of the active acoustic element to contact the heat exchanger. Such an embodiment may be beneficial in enabling heat to be extracted from different spatial regions of the active acoustic element 100. The two electrically conductive members 130 and 130' may be connected in parallel to a common electrode of the active acoustic element 130 or may contact different electrodes, such as a signal electrode and a ground electrode. For example, in some cases, a signal electrode and a ground electrode may be located at different spatial regions on the proximal surface 120 of the active acoustic element 100. FIG. 5B illustrates an alternative example embodiment in which multiple electrically conductive members (131 and 131') extend beyond the proximal surface 120 and merge into a common proximal electrically conductive segment 132 that contacts the heat exchanger 140.

Moreover, it will be understood that the electrically conductive member (or members) may take on a wide variety of possible shapes. In some example embodiments, at least a portion of the electrically conductive member (e.g. a portion of the electrically conductive member that contacts the heat exchanger) has a cylindrical profile (e.g. a pin). In other example embodiments, at least a portion of the electrically conductive member (e.g. a portion of the electrically conductive member that contacts the heat exchanger) has a planar surface, such as a foil or fin. In other example embodiments, at least a portion of the electrically conductive member (e.g. a portion of the electrically conductive member that contacts the heat exchanger) one or more lateral members (e.g. fins) extending laterally therefrom. In some example embodiments, the portion of the electrically conductive member that contacts the heat exchanger may have a cross-sectional diameter that varies along its length of contact with the heat exchanger. This cross-sectional area of this portion of the electrically conductive member may vary along its length and be greater or/or smaller than the cross-sectional area of the electrically conductive member at its distal end. In some example embodiments, the portion of the electrically conductive member that contacts the heat exchanger may be uneven, non-symmetric, rough and/or have extensions or other structures, shapes, or surface patterns or micro-structures to enhance heat transfer. It will be understood that the active acoustic element of the ultrasound transducer apparatus may be any suitable element that is capable of converting electrical signals into acoustic vibrations. Suitable example active acoustic elements may include piezoelectric materials, like lead zirconate titanate or lithium niobite, or capacitance-driven structures like CMUTs.

Figure 6A:
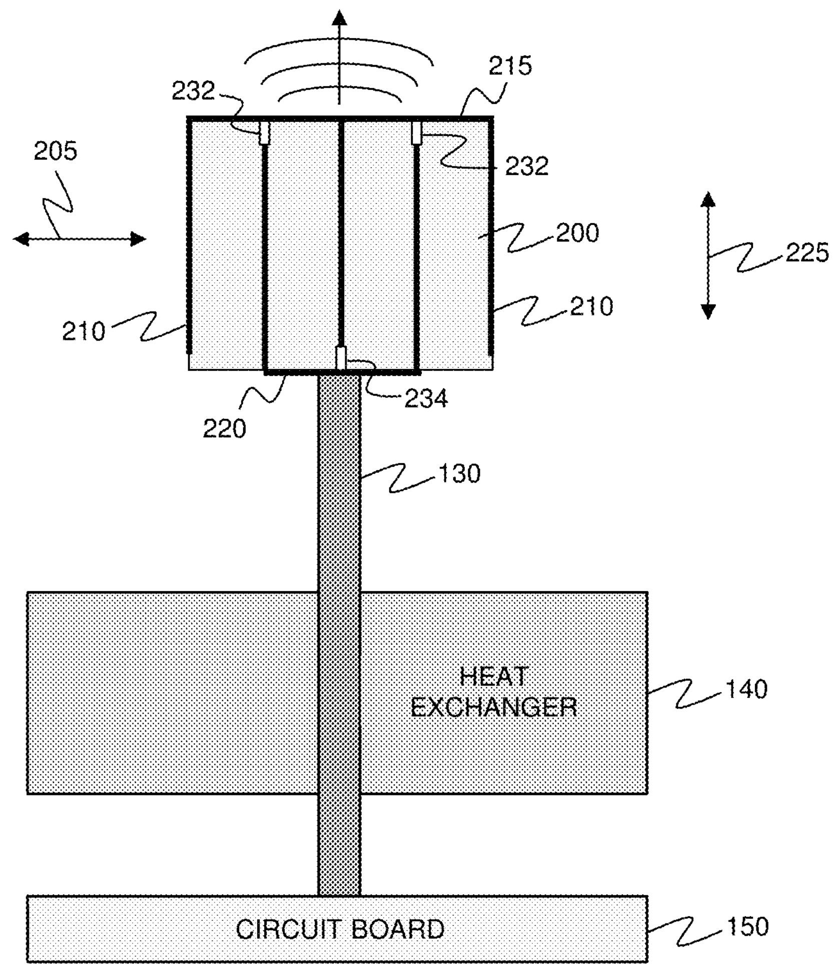
FIG. 6A shows a cross-sectional view of an example proximally-cooled ultrasound transducer apparatus in which the ultrasound transducer is a lateral-mode ultrasound transducer.

In some example embodiments, the active acoustic element may be a lateral-mode piezoelectric transducer formed from a stack of piezoelectric layers, with adjacent layers having opposing poling directions. Such an approach may be beneficial in avoiding the need for electrical matching circuits. An example of such a lateral-mode active acoustic element is shown in FIG. 6A, which illustrates a piezoelectric stack that includes a plurality of piezoelectric layers 200 stacked along a horizontal direction 205. The piezoelectric stack includes a plurality of electrodes that include a pair of outer electrodes 210 formed on respective outer lateral surfaces of the piezoelectric stack and a set of internal electrodes, with each internal electrode residing between adjacent piezoelectric layers of the piezoelectric stack. The piezoelectric stack also includes a first common electrode 215 in electrical communication with a first subset of the plurality of electrodes and a second common electrode 220 in electrical communication with a second subset of the plurality of electrodes. As can be seen in the figure, the first subset of electrodes and the second subset of electrodes are selected such that when a driving signal is applied between the first common electrode 215 and the second common electrode 220, the driving signal is applied in opposing directions among the neighbouring piezoelectric layers of the piezoelectric stack. Moreover, when the driving signal is applied at a frequency associated with a lateral mode coupled resonance of the piezoelectric stack, lateral mode coupling causes the piezoelectric stack to be mechanically responsive along a second direction (the distal-proximal vertical direction 225) that is perpendicular to the horizontal direction 205, thereby producing ultrasound emission along the vertical direction.

As shown in FIG. 6A, each internal electrode of the second subset of electrodes (the second and fourth electrodes) is electrically isolated from the first common electrode 215 by a respective electrically insulating channel 232 residing proximal to the distal surface and extending, from the distal surface, in a proximal direction, and each internal electrode of the first subset of electrodes (the single central electrode in the figure) is electrically isolated from the second common electrode 220 by a respective electrically insulating channel 234 residing proximal to the proximal surface and extending, from the proximal surface, in a distal direction.

Figure 6B:
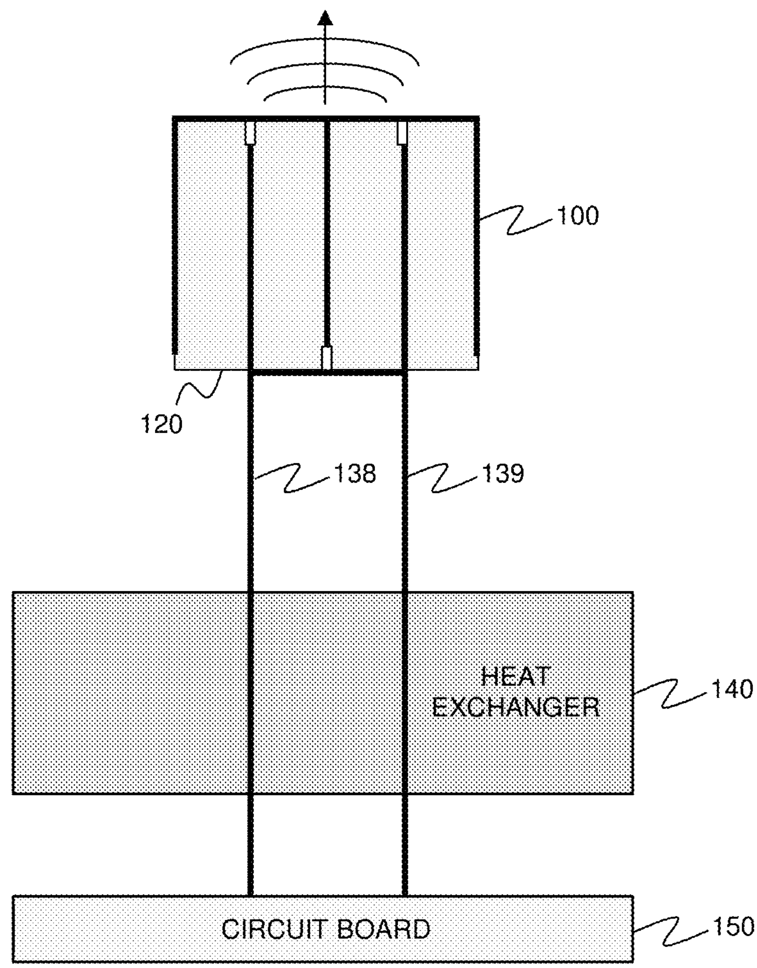
FIG. 6B shows a cross-sectional view of an example proximally-cooled ultrasound transducer apparatus in which the ultrasound transducer is a lateral-mode ultrasound transducer, where multiple electrodes of the lateral mode ultrasound transducer extend beyond the proximal surface and contact the heat exchanger.

In some example embodiments, one or more of the electrodes of the lateral mode active acoustic element may be formed from electrically conductive foils. In some example embodiments, one or more electrodes of the lateral mode ultrasound transducer may extend beyond the proximal surface of the active acoustic element to contact the heat exchanger, such that the one or more electrodes are employed for both providing electrical driving signals and for thermally conductive heat removal. An example of such an embodiment is illustrated in FIG. 6B, where two electrodes 138 and 139 of the example lateral mode active acoustic element extend proximally across a gap to contact the heat exchanger 140 and also contact the circuit board 150 (or a connector/cable) for the delivery of electrical driving signals.

In one example implementation, at least the internal electrodes of the lateral mode active acoustic element may be formed via an electrically conductive adhesive (e.g. electrically conductive epoxy) that is employed to join the multiple piezoelectric layers 200. The electrically insulating channels (e.g. channels 232 and 234 of FIG. 6A) may be formed within a given surface (e.g. proximal or distal) by dicing a thin trench adjacent along the initial portion of the internal electrode, thus removing it, and then filling the trench with an electrically insulating adhesive. The common electrode associated with the given surface may then be formed over the filled trench to connect the suitable like electrodes. This example method of fabricating a lateral mode active acoustic element ensures that the conductive adhesive layer for the signal electrodes does not touch the ground electrodes (e.g. on the left and right sides of the element in the case of an element with an even number of layers). Furthermore, unlike methods disclosed in U.S. Pat. No. 9,327,317, titled “Ultrasound transducer and method for making the same,” the present example method enables the fabrication of elements that can be readily assembled into two-dimensional arrays.

Traditional transducer manufacturing methods involve the processing of a large piece of transducer material that would remain together as a monolithic component to form the transducer array, with various processes performed to define the elements into the component. This conventional method is a top-down approach, where smaller features are defined into a large piece. In contrast to such methods, the multilayer lateral mode active acoustic elements may instead be formed processing a large piece of material to define a plurality of individual elements (such a method has been found to be capable of producing approximately 300 elements at a time). For example, individual acoustically active plates (piezoelectric layers 200 in FIG. 6A, for example, with a size of approximately 40 mm×40 mm), may be glued together with conductive epoxy to form a large multi-layer plate (stack). This plate may then be processed into smaller elements (e.g. with sizes of approximately 1.3 mm×3.2 mm). The third dimension of the elements is dependent on the thickness of the stack of plates (the plate thickness, epoxy thickness, and number of plates).

This approach produces individual loose elements that can be assembled as individual parts into an arbitrary array geometry. This bottom-up approach employs individual small pieces to build the larger part array. The bottom-up assembly approach is not limited to these types of elements. It applies to any transducer element that can be tested, manipulated, and assembled as an individual component. For example, thickness mode elements, non-layered elements, or tube-shaped elements could be used with this assembly technique.

Figure 7:
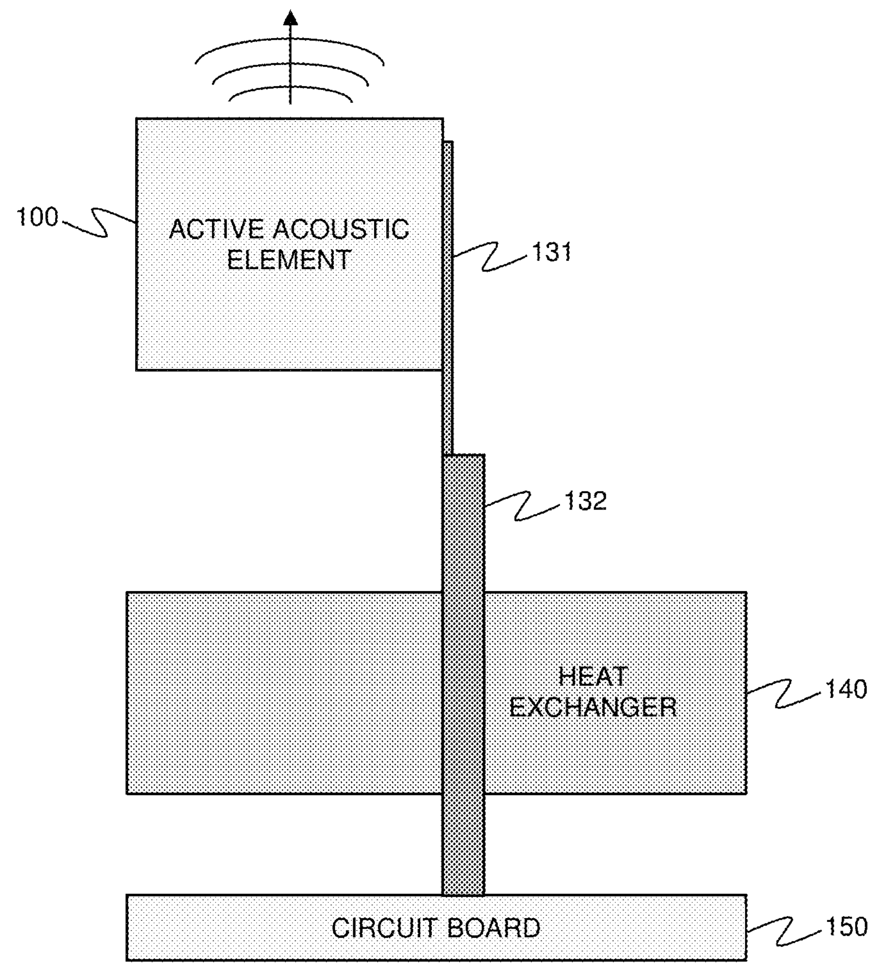
FIG. 7 shows a cross-sectional view of an example proximally-cooled ultrasound transducer apparatus in which the electrically conductive member contacts a lateral surface of the acoustically active element and extends, in a proximal direction, beyond the proximal surface of the acoustically active element to contact the heat exchanger.

Although many of the preceding example embodiments involving the contact of an electrically conductive member with a proximal surface of the active acoustic element, it will be understood that other example embodiments may be provided in which the electrically conductive member contacts a lateral surface of the active acoustic element. One example embodiment is shown in FIG. 7, in which the electrically conductive member contacts a lateral surface of the acoustically active element and extends, in a proximal direction, beyond the proximal surface of the acoustically active element to contact the heat exchanger 140. In the example embodiment shown in the figure, the electrically conductive member includes a distal segment 131 and a proximal segment 132, where the distal segment 131 contacts the lateral surface of the active acoustic element and the proximal segment 132 extends from the distal segment 131 to contact the heat exchanger 140. In the example embodiment shown in the figure, at least the distal segment 131 (and optionally the proximal segment) has planar surfaces. Unlike some of the previously described and illustrated example embodiments that involve contact of the electrically conductive member with the proximal surface of the active acoustic element 100, the present example embodiment may be advantageous in that the proximal surface is free from contact with the electrically conductive member, which may be beneficial in increasing the output power and mechanical response of the ultrasound transducer.

Figure 8:
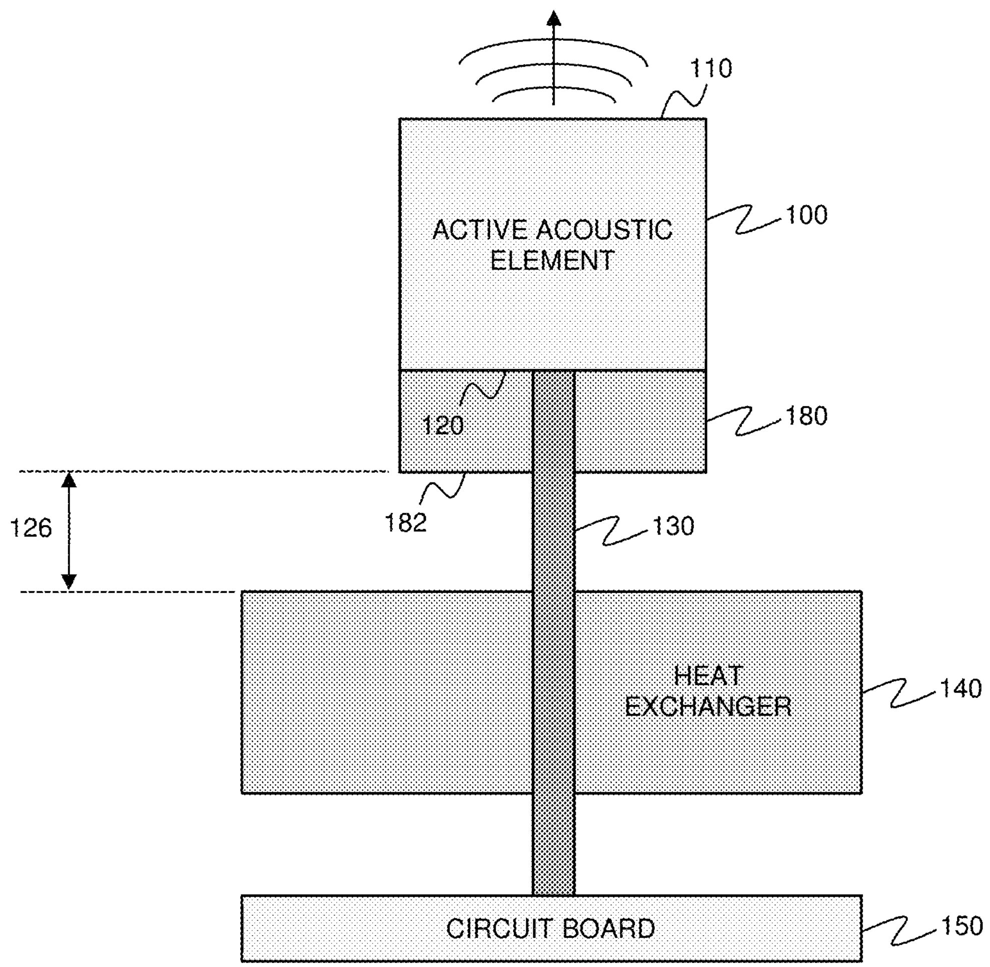
FIG. 8 illustrates an example embodiment of a proximally-cooled ultrasound transducer apparatus in which the proximal surface of the acoustically active element is contacted, over a region that does not contact the electrically conductive member, by an additional material, such that the electrically conductive member extends in the proximal direction through the material before contacting the heat exchanger. The material may be selected to have an impedance match or mismatch with the active acoustic element for transmitting or reflecting ultrasound energy at the proximal surface of the acoustically active element, respectively.

Although the preceding example embodiments have shown example configurations in which the portion of the proximal surface that does not contact the electrically conductive member is absent from contact with another liquid or solid material or medium, it may be beneficial for the proximal surface to contact another material in some cases. An example of such an embodiment is illustrated in FIG. 8, where a material 180 is shown contacting the proximal surface 120 of the active acoustic element 100, and where the electrically conductive member 130 is shown extending from the proximal surface 120, through the material 180, before contacting the heat exchanger 140. While the figure illustrates an example implementation in which a gap 126 exists between the proximal surface 182 of the material, it will be understood that the gap may be absent, such that the proximal surface 182 of the material directly contacts the heat exchanger 140, optionally to facilitate additional heat removal through the material 180, in addition to the heat that is removed through the electrically conductive member 130.

For example, in cases in which it is desirable for backward-propagating ultrasound energy generated within the active acoustic element to be reflected at the proximal surface (e.g. to increase the acoustic output power from the distal surface), the proximal surface may be contacted with a material having an acoustic impedance that is mismatched with that of the active acoustic element. For example, the acoustic impedance of the material may be selected such that at least 50%, but preferably more than 90% or 99%, of the backward-propagating ultrasound energy is reflected at the proximal surface. Examples of suitable materials for enhancing acoustic reflection include air or other gasses, or a multi-layer matching structure of tuned thicknesses.

For example, if the ultrasound apparatus is employed for an imaging application, it may be desirable to prevent or at least partially suppress reflections, at the proximal surface, of backward-propagating ultrasound energy generated within the active acoustic element. This may be achieved, for example, by contacting the proximal surface with an acoustically attenuating material having an acoustic impedance that is selected to prevent or reduce reflections at the proximal surface. For example, the acoustic impedance of the material may be selected such that less than 50%, but preferably less than 10%, of the backward-propagating ultrasound energy is reflected at the proximal surface. This material may also have high acoustic attenuation. Examples of suitable backing materials for imaging applications include silicone or epoxy, either possibly loaded with powder.

Figure 9:
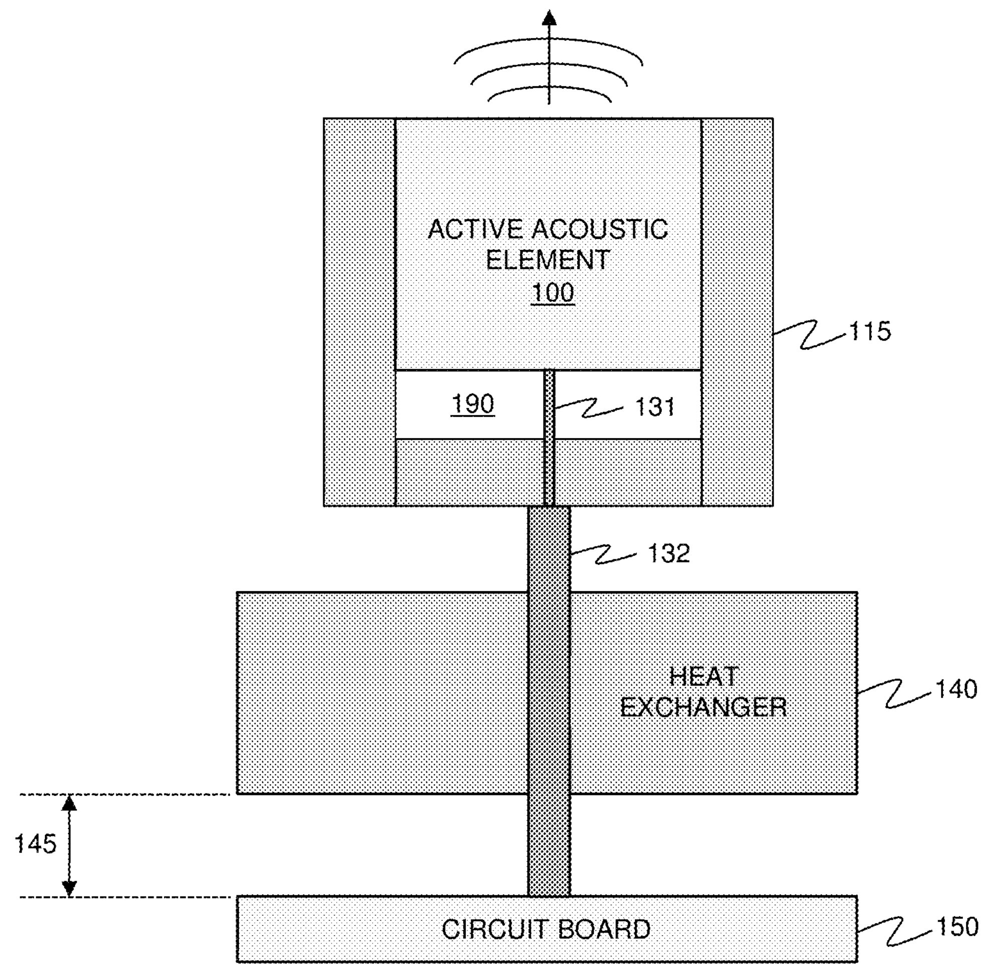
FIG. 9 shows a cross-sectional view of an example proximally-cooled ultrasound transducer apparatus in which the ultrasound transducer is received within a housing, illustrating an example configuration in which the housing supports the ultrasound transducer such that a gap resides between the proximal surface of the active acoustic element of the ultrasound transducer and the housing, with the electrically conductive member extending across the gap.

In some example embodiments, the active acoustic element may be supported by a housing. An example embodiment is shown in FIG. 9, in which the active acoustic element 100 is received and supported within a housing 115. As illustrated in the figure, the housing 115 may support the active acoustic element 100 and may also optionally support at the electrically conductive member such that a gap 190 resides between the proximal surface of the active acoustic element and the housing, with the electrically conductive member extending across the gap.

Figure 10A:
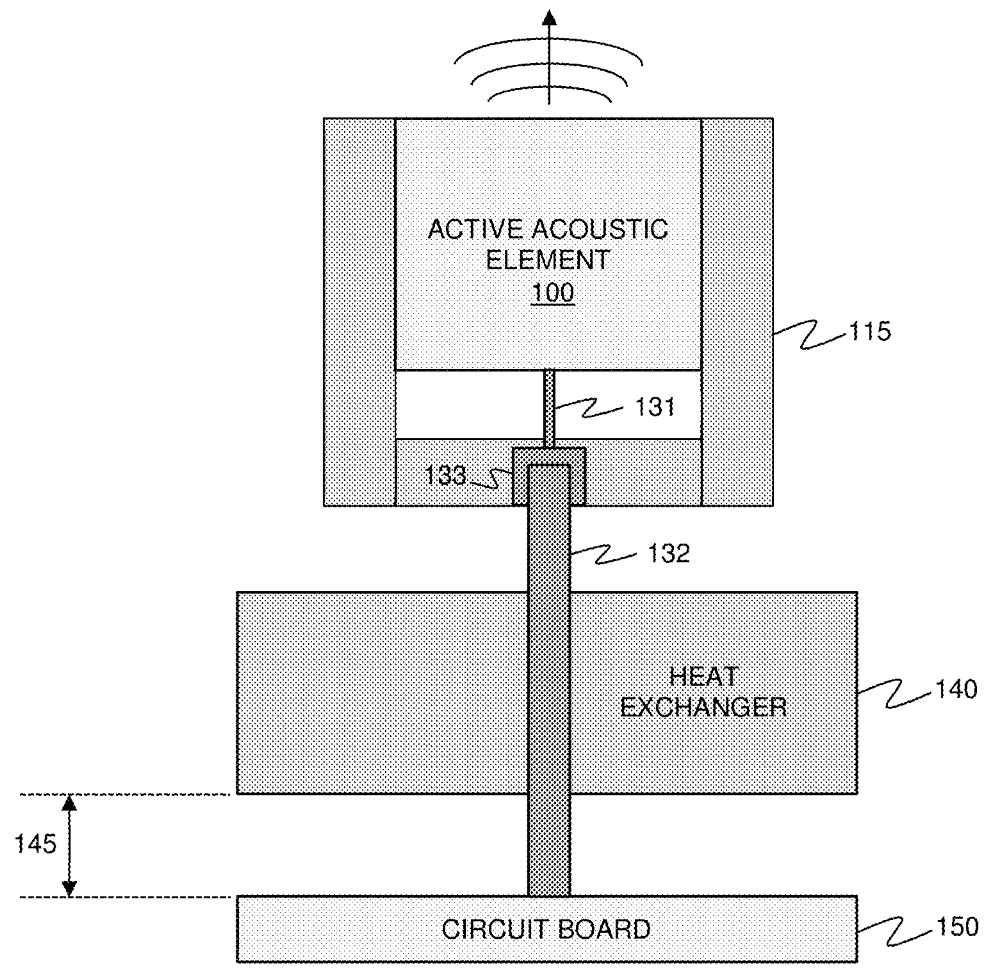
FIGS. 10A and 10B show a cross-sectional view of an example proximally-cooled ultrasound transducer apparatus in which the electrically conductive member includes a first segment that is detachably connected to a second segment, illustrating an example configuration in which the ultrasound transducer and the first portion of the electrically conductive member are supported by a housing.
Figure 10B:
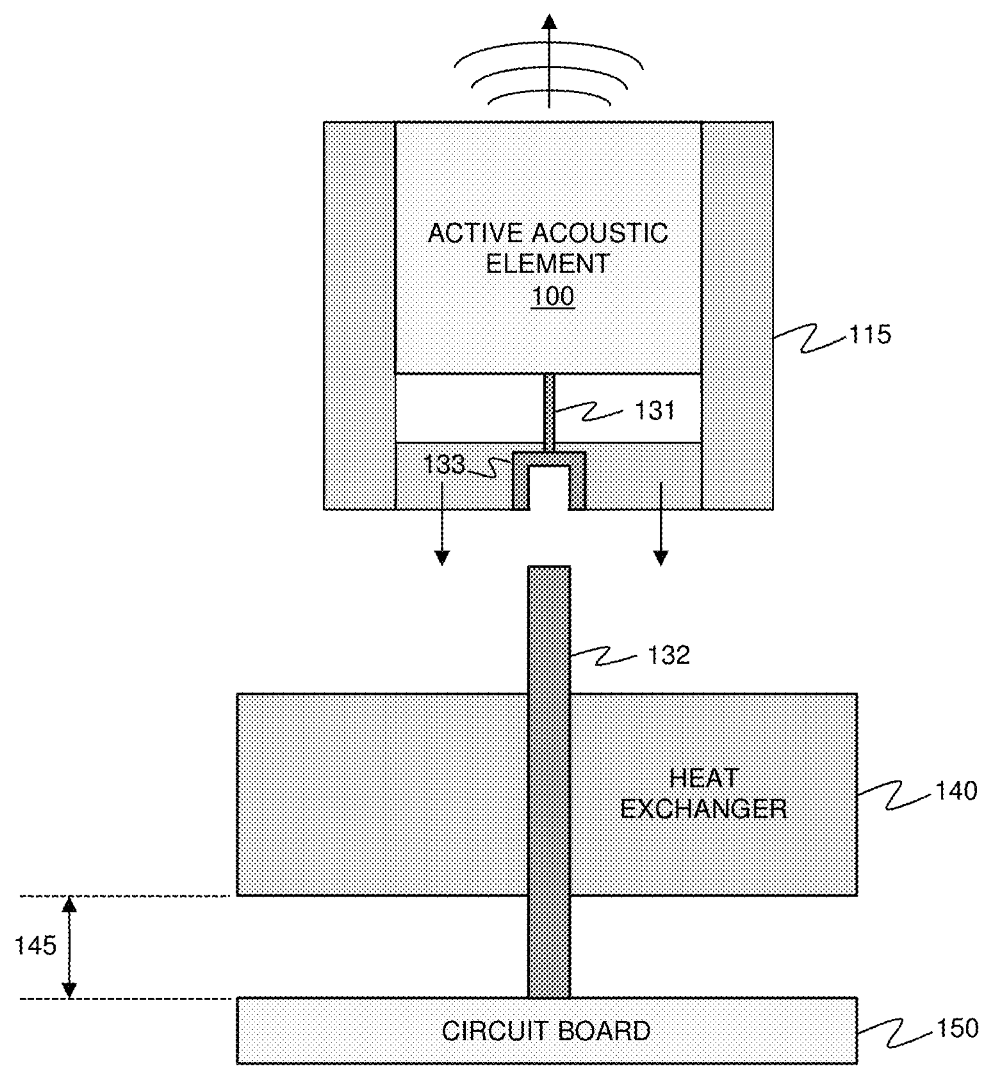

FIG. 9 illustrates an example embodiment in which the electrically conductive member includes a first segment 131 and a second segment 132. The first segment 131 may be supported by the housing 180, such that the distal end or region of the first segment 131 contacts the active acoustic element 100. In some example embodiments, the second segment 132 may be supported by the heat exchanger 140. In such a case, the distal end of the second segment 132 may be removably connectable to a proximal end of the first segment 131, thereby facilitating a modular design in which the active acoustic element 100 can be fabricated, incorporated into the housing 115, and contacted with the first segment, and optionally tested prior to assembly with the heat exchanger 140. An example of this embodiment is illustrated in FIGS. 10A and 10B, in which the electrically conductive member includes a first segment 131 that is detachably connected to a second segment 132. In one example embodiment, one or both of the housing 115 and the heat exchanger may support a socket that facilitates connection between the first segment 131 and the second segment 132. FIGS. 10A and 10B show an example configuration in which the housing supports a socket 133 that is electrically connected to, or monolithically formed with, the first segment 131, and which is configured to receive the distal end of the second segment 132. FIG. 10A shows the connected state, while FIG. 10B shows the disconnected state.

Figure 11:
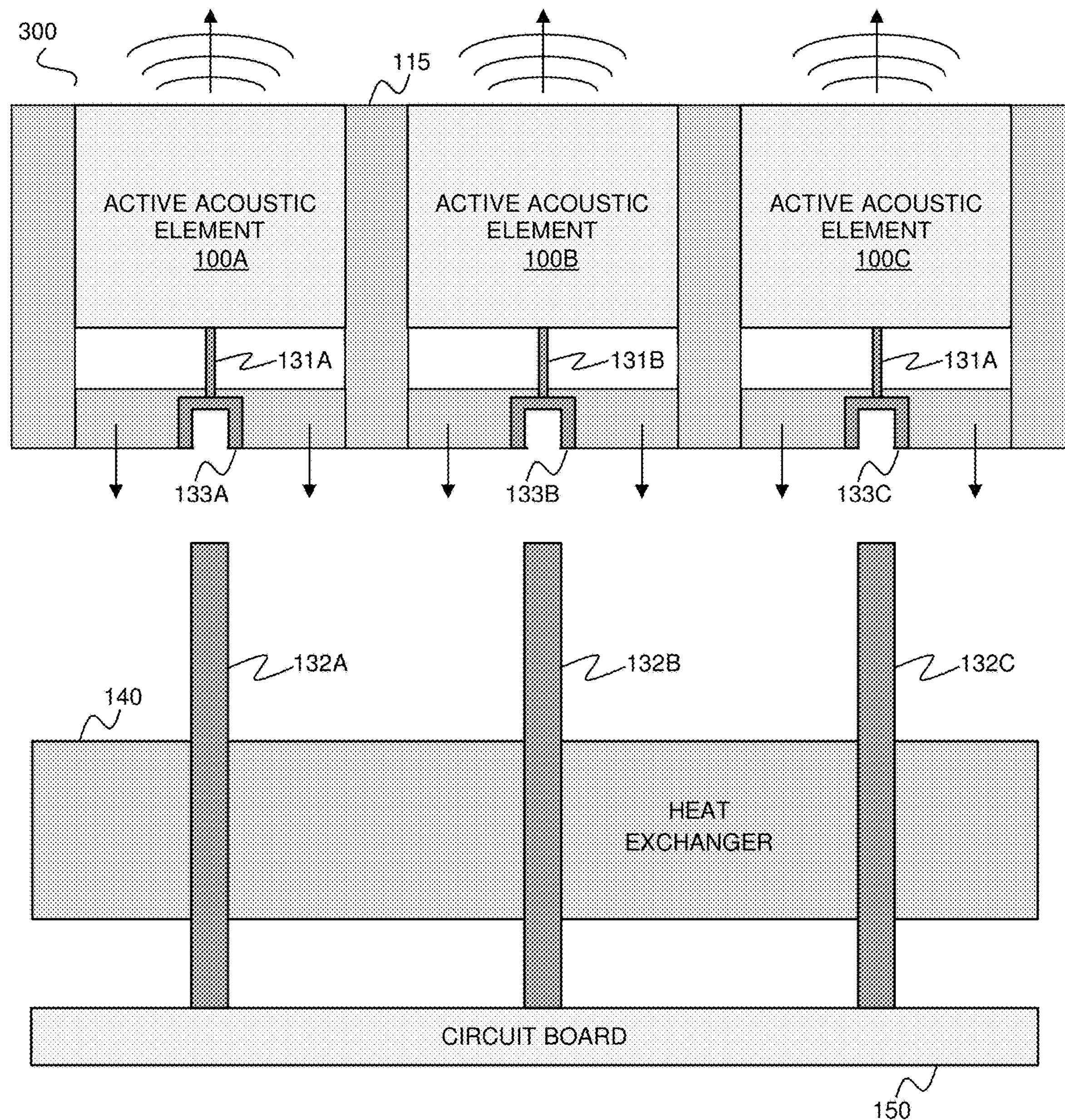
FIG. 11 illustrates an example embodiment in which an array of ultrasound transducer array elements are proximally-cooled via per-element electrically conductive members that contact a common heat exchanger, where each electrically conductive member includes a first segment, and where each active acoustic element and each first portion of the electrically conductive members is supported by a housing to form an array module. Each electrically conductive member also includes a second segment that contacts and is supported by the heat exchanger to form a cooling array that is detachably connectable to the array module.

FIG. 11 illustrates an example embodiment in which an array of active acoustic elements 100A-100C are proximally cooled via respective per-element electrically conductive members that contact a common heat exchanger 140. As in the example embodiment shown in FIGS. 10A and 10B, each electrically conductive member includes a first segment 131A-131C that contacts a socket 133A-133C supported by a common housing 115. The housing 115, the first electrically conducive segments 131A-131C and the sockets 133A-133C form an ultrasound array module 300. The heat exchanger 140 supports an array of second electrically conductive segments 132A-132C, such that the array of second electrically conductive segments 132A-132C form a cooling array that is detachably connectable to the array module.

The circuit board 150 may be replaced with a connector or cable, or may be a flexible printed circuit board consisting of electrical traces for delivering electrical driving signals to the active acoustic elements 100A-100C, where the electrical traces may be separated and shielded by common ground traces. The electrical traces may reside on multiple layers of the printed circuit board 150. One end of the printed circuit board 150 may include connectors that match the locations of the electrically conductive members. The other end of the flex cable is connected to, or connectable to, the drive electronics.

Figure 12:
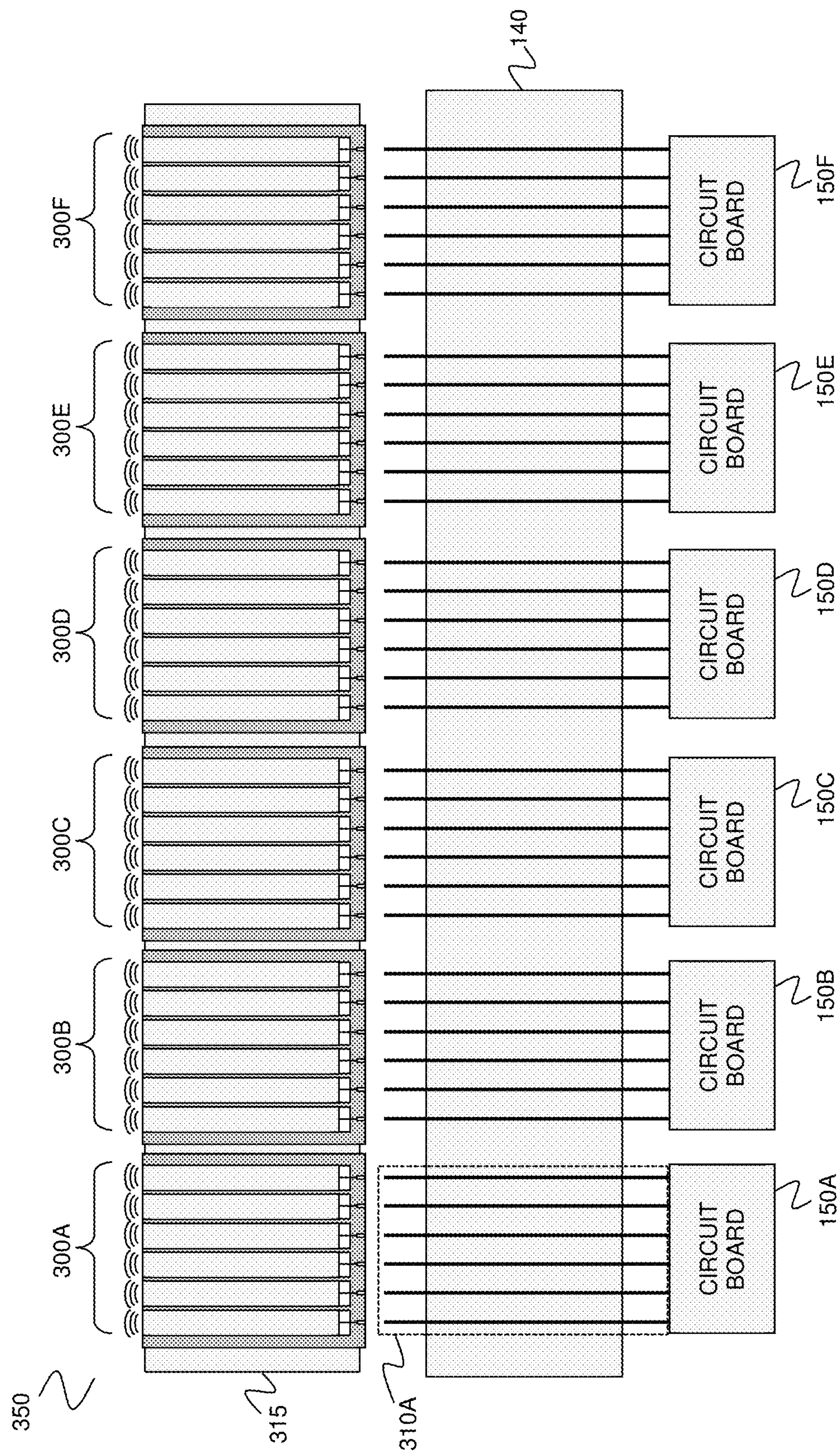
FIG. 12 illustrates an example embodiment in which a plurality of array modules are detachably connected to respective cooling arrays contacting a common heat exchanger.

In some example embodiments, a plurality of array modules 300 may be arranged such that each array module defines a sub-array of active acoustic elements that together form an ultrasound array. An example of such an embodiment is illustrated in FIG. 12, in which array modules 300A-300F are arranged and supported by a common frame 315. As shown in the figure, the first electrically conductive elements that extend from the proximal surface of each active acoustic element of each array module are detachably connectable to respective cooling arrays (one such array, configured to detachably connect with array module 300A, is shown at 310A) defined by arrays of second electrically conductive elements that contacting the common heat exchanger 140. While the array modules may be connected, through their corresponding electrically conductive members, to a common circuit board, FIG. 12 illustrates an example embodiment in which each array module 300A-300F is connected to a per-module circuit board 150 (or per-module connector or cable). Each per-array-module circuit board 150 may support, or may be connected to, or connectable to, respective per-array-module drive electronics. As explained in more detail below, such an example embodiment facilitates the use of a separate remote cooling assembly for the drive electronics that correspond to each array module.

Figure 13:
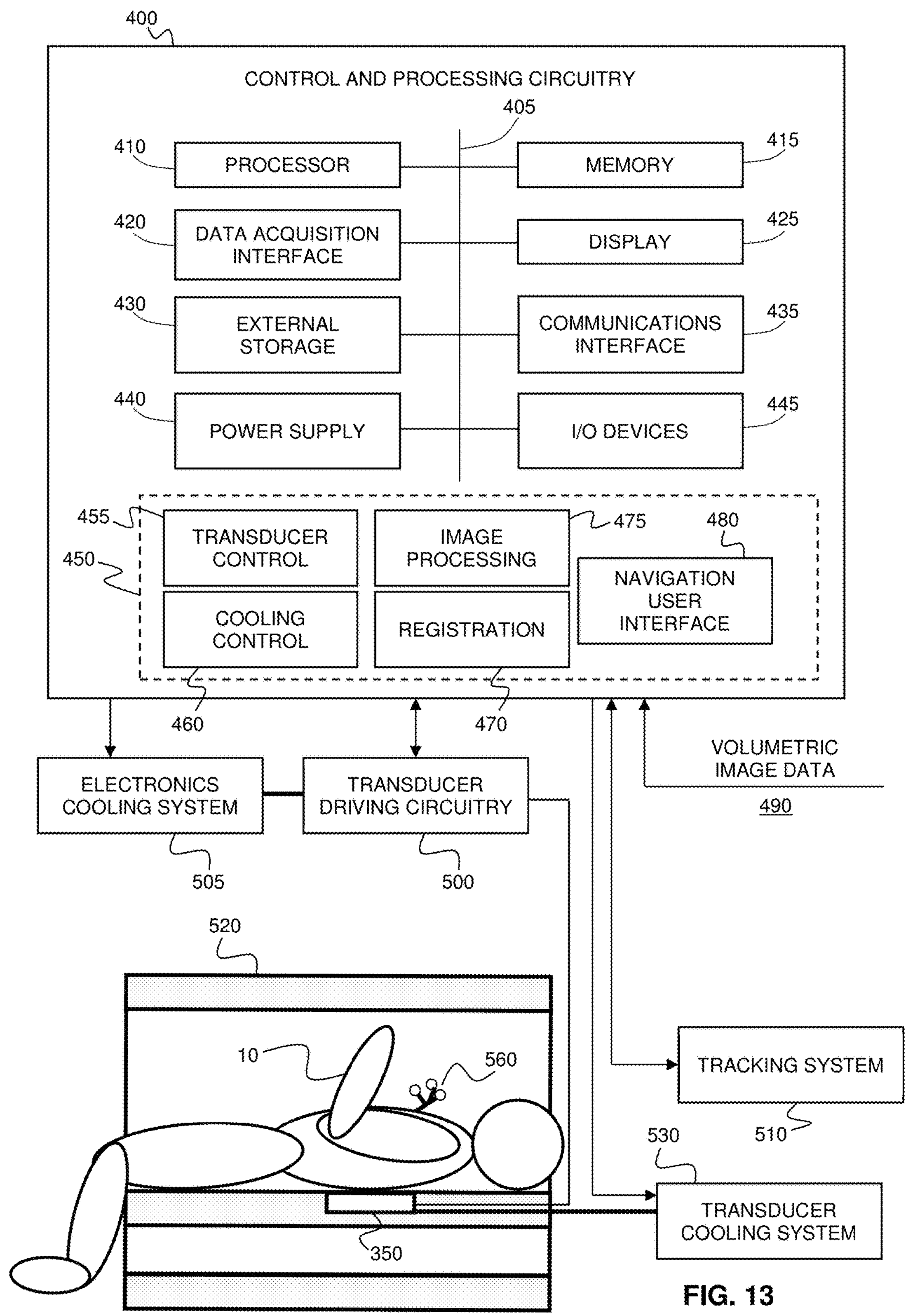
FIG. 13 schematically illustrates an example system for performing ultrasound therapy or imaging using a proximally-cooled ultrasound transducer apparatus.

FIG. 13 is a block diagram illustrating an example system for performing diagnostic and/or therapeutic ultrasound procedures. The control and processing circuitry 400 is operably connected to an ultrasound transducer array 350 via the transducer driver electronics/circuitry 500, which delivers electrical signals for to the ultrasound transducer array 350 for generating and emitting ultrasound energy. The ultrasound transducer array is proximally cooled according to the example embodiments described herein and the example system illustrates the use of a exchanger connected to an external transducer cooling system that recirculates an electrically insulating fluid, where electrically insulating fluid flows through a heat exchanger that is contacted via the electrically conductive members extending from the active acoustic elements of the ultrasound array. The transducer cooling system 530 may include a pump, an optional temperature sensor, a fluid reservoir, and/or a cooling device (e.g. a thermo-electric cooler or a heat sink) and may be operably connected to, and controlled by, the control and processing circuitry 400.

The transducer driver electronics/circuitry 500 may include, for example, but is not limited to, Tx/Rx switches, transmit and/or receive beamformers. For example, a transmit/receive switch may be included receive reflected ultrasound energy signals detected by the ultrasound transducer array 350. The transducer driver electronics circuitry may be cooled via the electronics cooling system (e.g. an active heat exchanger, such as a forced fluid flow heat exchanger or a thermo-electric cooler) that may be operably connected to, and controlled by, the control and processing circuitry 400.

In example embodiments in which the ultrasound transducer array 350 includes a plurality of array modules (such as those described above), each array module may be interfaced with separate and dedicated driving electronics, and each of the separate and dedicated driving electronics may have a respective electronics cooling system (e.g. a dedicated thermoelectric cooler and heat sink). For example, each array module may be operably connected to one or more application specific integrated circuits (ASICs) with multiple (e.g. 64) channels, each channel capable of generating independent outputs. The ASICs may be connected, via flexible printed circuit boards, to amplifiers for the amplification of the respective ASIC outputs. The ASICs and amplifiers may be mounted to heat sinks and cooled by forced air circulation or cooled liquid. Multiple ASICs may be connected through a backplane to a common per-array-array module controller, and multiple per-array-module-controllers may be connected (e.g. through a network) to the control and processing circuitry 400 such that they are synchronized by a common clock. In one example embodiment, at least a portion of the driving electronics may be housed or encased within a Faraday cage (e.g. a Faraday cage having a high-pass cutoff frequency above the operation bandwidth of a magnetic resonance scanning device employed during an ultrasound procedure involving the ultrasound array).

The control and processing circuitry 400, which includes one or more processors 410 (for example, a CPU/microprocessor), bus 405, memory 415, which may include random access memory (RAM) and/or read only memory (ROM), a data acquisition interface 420, a display 425, external storage 430, one more communications interfaces 435, a power supply 440, and one or more input/output devices and/or interfaces 445 (e.g. a speaker, a user input device, such as a keyboard, a keypad, a mouse, a position tracked stylus, a position tracked probe, a foot switch, and/or a microphone for capturing speech commands).

The control and processing circuitry 400 may be programmed with programs, subroutines, applications or modules 450, which include executable instructions, which when executed by the one or more processors 410, causes the system to perform one or more methods described in the present disclosure. Such instructions may be stored, for example, in memory 415 and/or other storage.

In the example embodiment shown, the transducer control module 455 includes executable instructions for controlling the transducers of the ultrasound transducer array 350 to deliver energy to a target location or region of interest. In some example implementations, the delivery of ultrasound energy to a target location may be based on the registration of the transducer positions and orientations with volumetric image data 490. For example, the ultrasound array 350 may support a plurality of phased-array transducers, and transducer control module 455 may control the beamforming applied (on transmit and/or receive) to deliver, based on the known positions and orientations of the phased array transducers relative to the volumetric image data 490, one or more focused energy beams to a region of interest. The region of interest may be specified intraoperatively by a user (e.g. via a user interface controlled by control and processing circuitry 400) or according to a pre-established surgical plan.

In the example system, a registration module 470 may optionally be employed for registering volumetric image data 490 to an intraoperative reference frame associated with a tracking system 510. The volumetric image data 490 and registration data associated with the positions of the ultrasound transducer array may be stored on an external database or stored in memory 415 or storage 430 of control and processing circuitry 400.

The optional image processing module 475 may be employed to generate ultrasound images by processing ultrasound signals detected by the ultrasound transducer array (e.g. by performing receive beamforming on a set of received ultrasound signals). The optional navigation user interface module 480 includes executable instructions for displaying a user interface showing spatially registered volumetric images for image-guided procedures.

The tracking system 510 may optionally be employed to track the position and orientation of the patient, via detection of one or more fiducial markers 560 attached to the patient 10, and optionally one or more medical instruments or devices also having fiducial markers attached thereto. For example, passive or active signals emitted from the fiducial markers may be detected by a stereographic tracking system employing two tracking cameras.

As shown in the figure, the example system may be configured for use with a magnetic resonance imaging scanner 520. For example, the ultrasound array 350 may be fabricated from magnetic resonance imaging compatible materials and the electrical circuit boards and/or cables that deliver the drive signals to the ultrasound transducer array may be electrically shielded.

In some example embodiments, intraoperative volumetric image data may be obtained via the magnetic resonance imaging scanner, and a known spatial relationship (registration) between the ultrasound transducer array 350 and the magnetic resonance imaging scanner 520 may be employed to facilitate the intraoperative control of the focusing of therapeutic ultrasound energy at a desired target location during a therapeutic focused ultrasound procedure. The target location may be determined based on the intraoperative images, optionally by performing image registration between the intraoperative magnetic resonance images and pre-operative volumetric images associated with a surgical plan. In some example embodiments, intraoperatively acquired magnetic resonance images may be intraoperatively registered and displayed with intraoperatively acquired ultrasound images obtained via the ultrasound array 350 to facilitate the intraoperative monitoring of a therapeutic focused ultrasound procedure according to multiple image modalities.

Although only one of each component is illustrated in FIG. 13, any number of each component can be included in the control and processing circuitry 400. For example, a computer typically contains a number of different data storage media. Furthermore, although bus 405 is depicted as a single connection between all of the components, it will be appreciated that the bus 405 may represent one or more circuits, devices or communication channels which link two or more of the components. For example, in personal computers, bus 405 often includes or is a motherboard. Control and processing circuitry 400 may include many more or less components than those shown.

The control and processing circuitry 400 may be implemented as one or more physical devices that are coupled to processor 410 through one of more communications channels or interfaces. For example, control and processing circuitry 400 can be implemented using application specific integrated circuits (ASICs). Alternatively, control and processing circuitry 400 can be implemented as a combination of hardware and software, where the software is loaded into the processor from the memory or over a network connection.

Some aspects of the present disclosure can be embodied, at least in part, in software, which, when executed on a computing system, transforms a computing system into a specialty-purpose computing system that is capable of performing the methods disclosed herein. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases “computer readable material” and “computer readable storage medium” refer to all computer-readable media, except for a transitory propagating signal per se.

EXAMPLES

The following examples are presented to enable those skilled in the art to understand and to practice embodiments of the present disclosure. They should not be considered as a limitation on the scope of the disclosure, but merely as being illustrative and representative thereof.

The present example is provided to illustrate various aspects of the present disclosure through a non-limiting example embodiment of an ultrasound system that incorporates multiple ultrasound array modules, with each array module defining a sub-array of active acoustic elements, where the array modules are assembled to form an ultrasound array that is proximally cooled via common heat exchanger, as previously described with reference to FIG. 12.

Figure 14A:
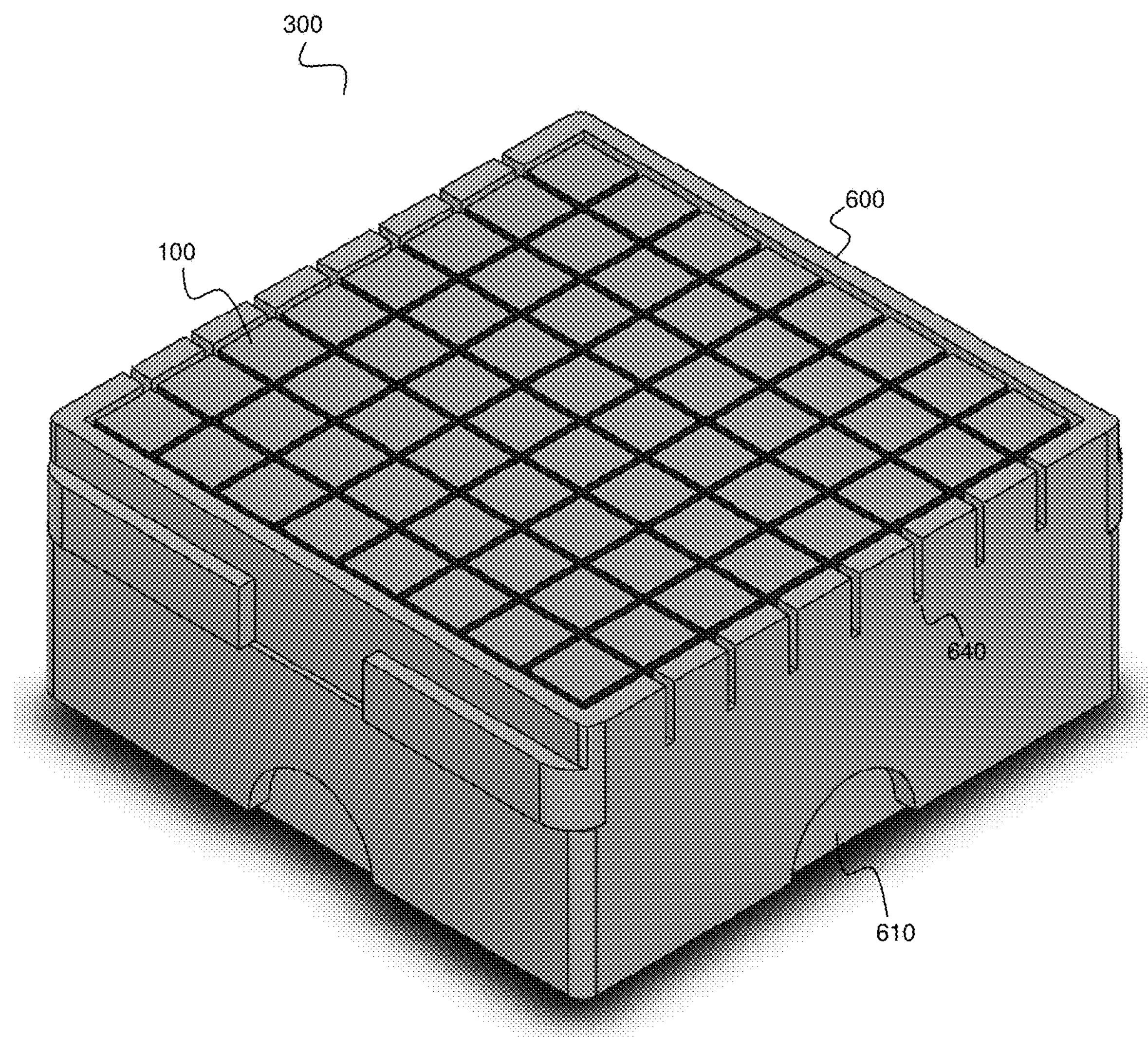
FIG. 14A-14F illustrate an example ultrasound array module that is connectable to a cooling array of a heat exchanger and a circuit board for cooling and delivery of electrical driving signals.
Figure 14B:
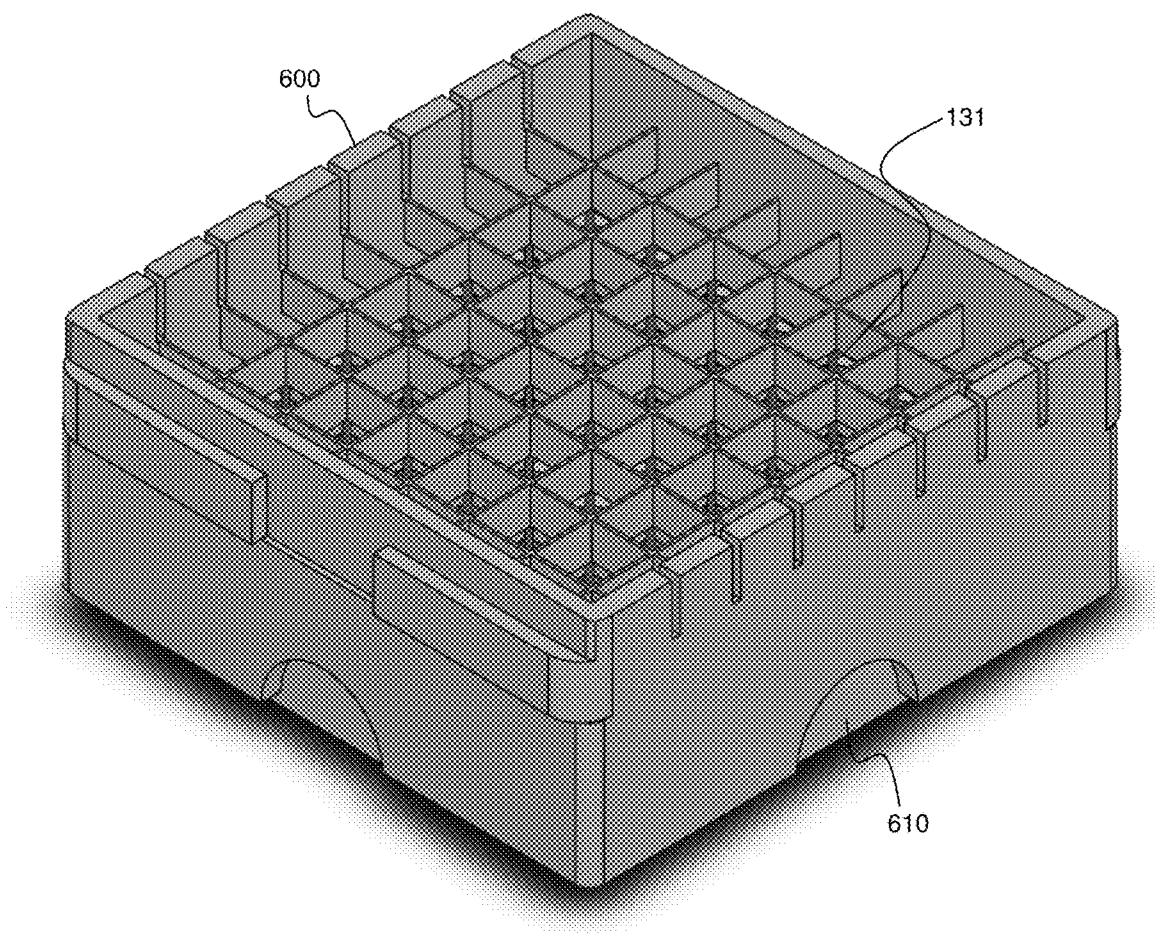
Figure 14C:
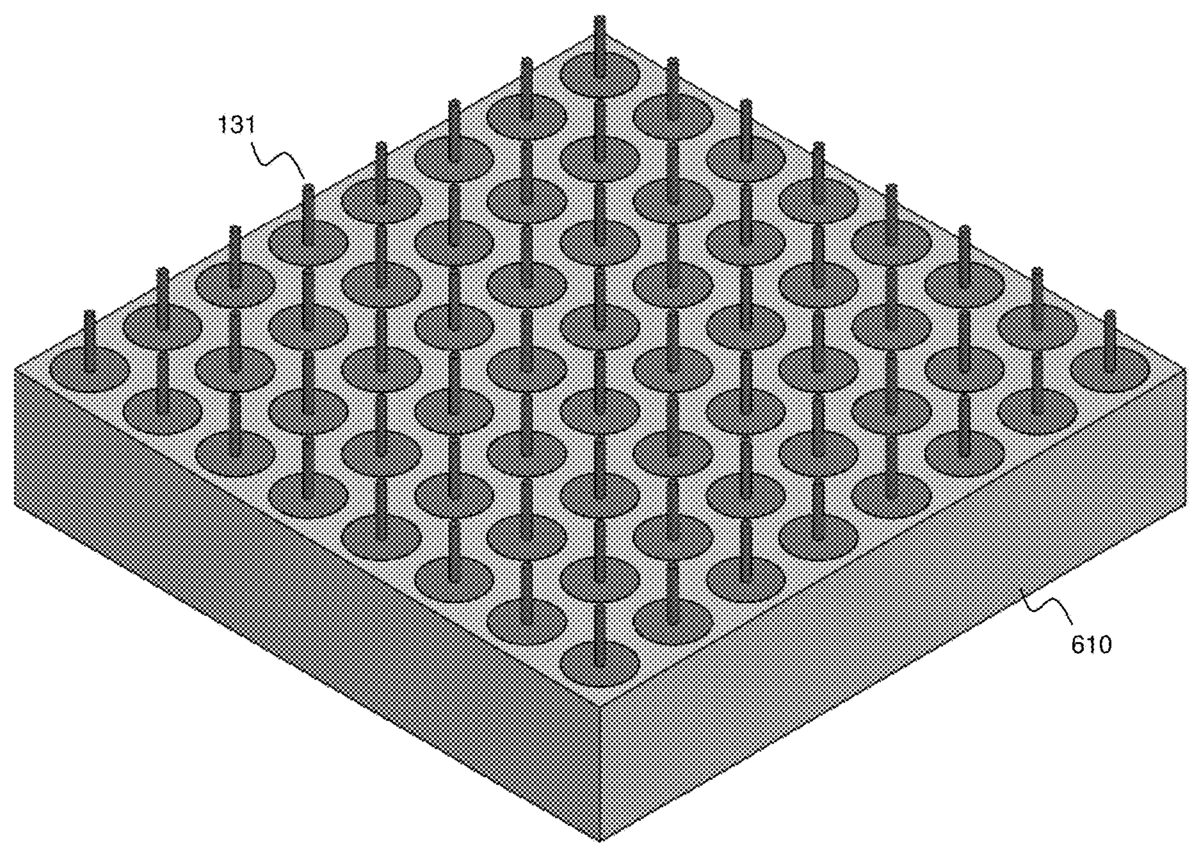

An example ultrasound array module 300 for use in assembling a larger ultrasound array system is shown FIG. 14A. The example array module 300 includes an array module housing that supports a plurality of active acoustic elements 100 in a two-dimensional sub-array. The example module housing includes two components, namely an electrically insulating grid frame 600 for supporting the active acoustic elements 100 in a spaced configuration forming the two dimensional sub-array, and an electrically insulating insert 610 that is received within an aperture formed in the underside of the grid frame 600 and recessed within the grid frame 600. The insert 610 supports the array of first segments 131 of the electrically conductive members, as shown in more detail in FIG. 14C. FIG. 14B shows the grid frame 600 prior to insertion of the active acoustic elements, showing the array of first segments 131 of the electrically conductive members that is supported by the insert 610.

Figure 14D:
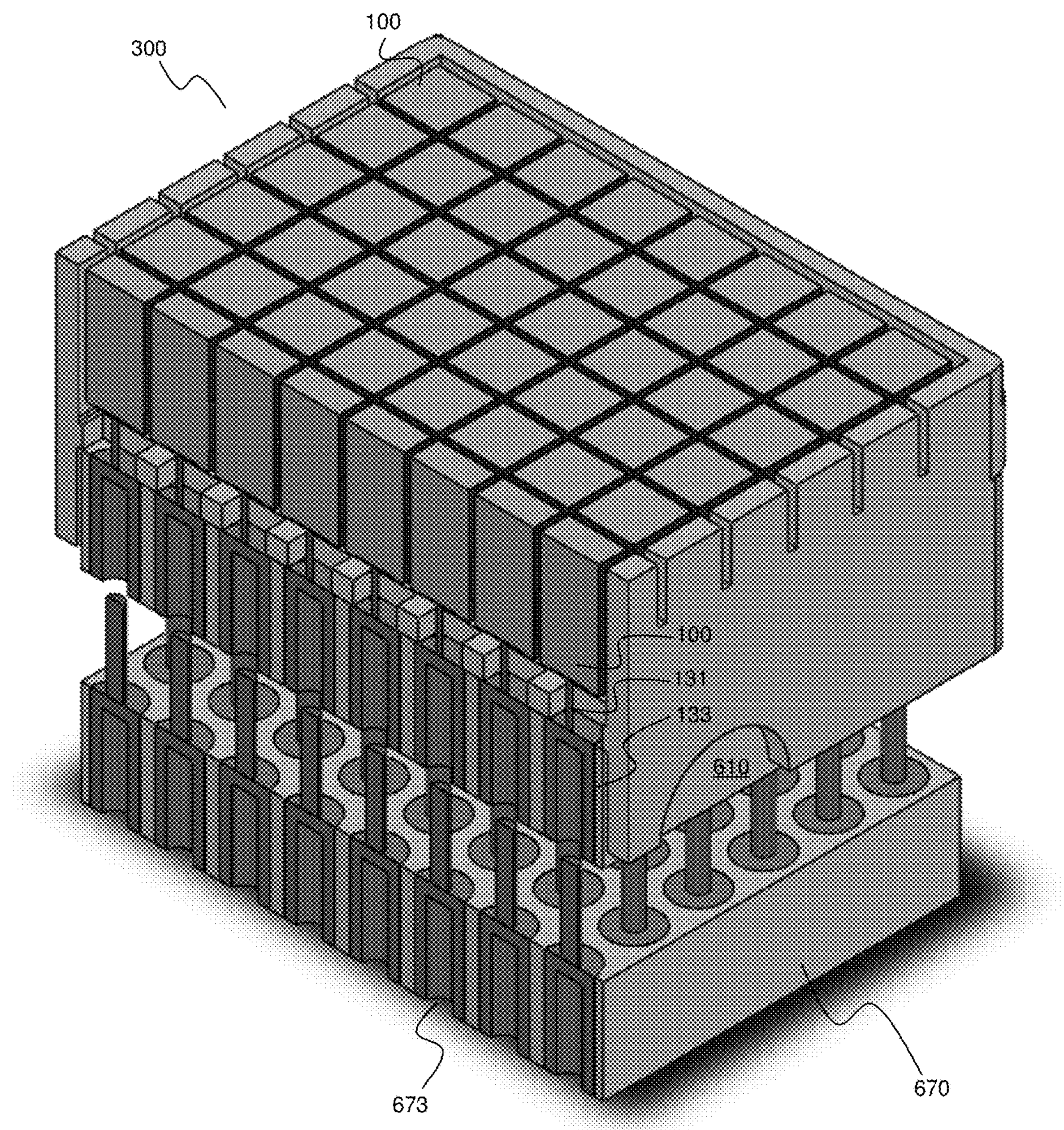
Figure 14E:
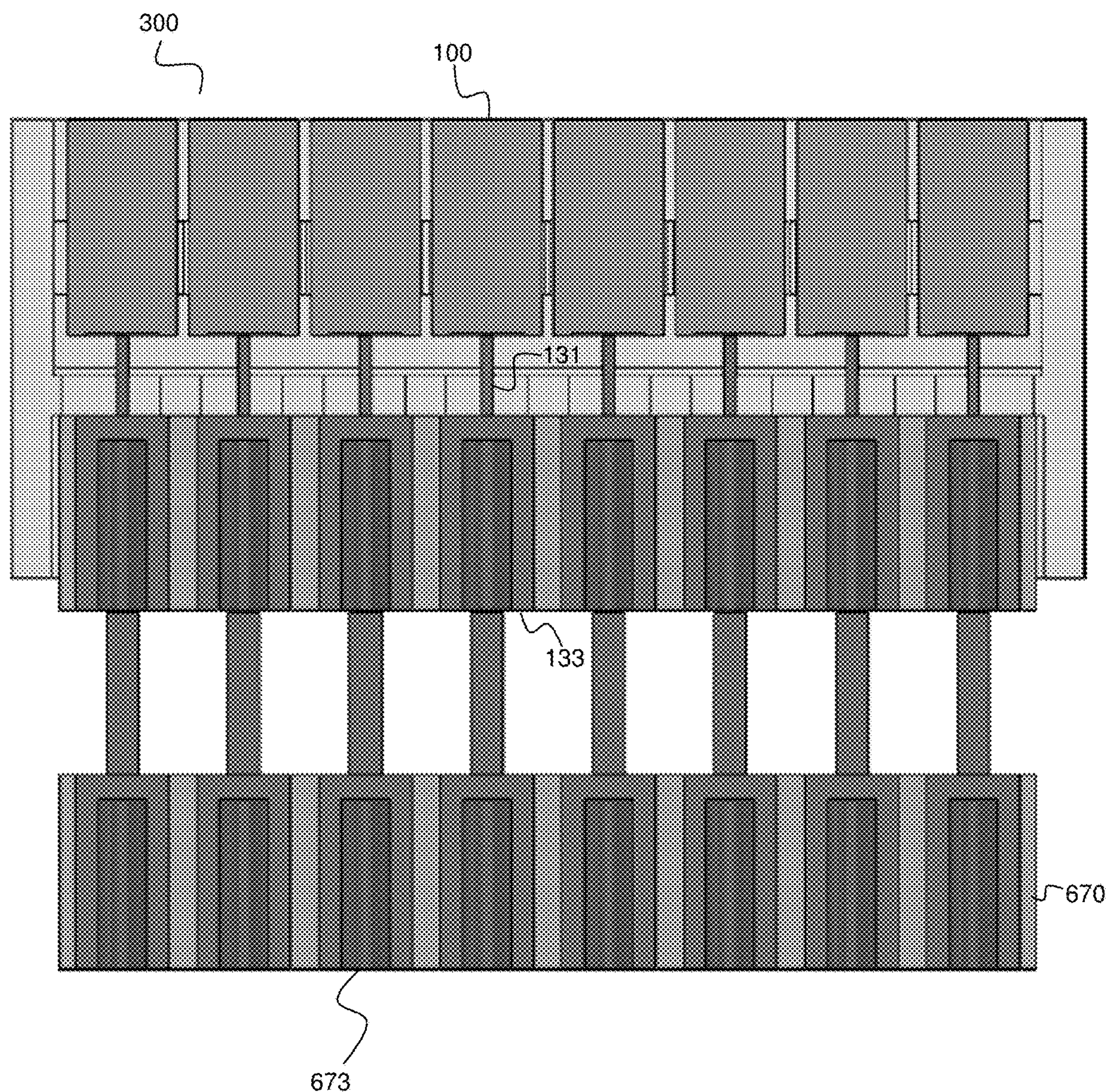

FIGS. 14D and 14E show a cross-sectional view of the array module. As can be seen in the figure, the first segments 131 of the electrically conductive members are supported by the inset 610 such that each first segment 131 contacts the proximal surface of a respective active acoustic element 100 and such that the first segment is capable of providing electrical drive signals to the active acoustic element 100 while also removing heat from the active acoustic element 100 via thermal conduction. As also shown in FIG. 14D, the insert 610 also supports the sockets 133 that are in electrical contact with respective first segments of the electrically conductive members the for receiving the distal end portions of the second segments of the electrically conductive members.

At the distal end of the device, ground connections may be provided by a thin metal wire or foil residing between the active acoustic elements and contacting the ground electrodes of each element (e.g. with a conductive adhesive such as conductive epoxy), thereby forming a common ground connection. In one example embodiment, the common ground connection can be implemented by foil residing between the rows of active acoustic elements. Other non-limiting example embodiments include (i) contacting an electrically conductive film with the distal surfaces of the active acoustic elements (which may also serves as waterproofing), employing an array of spring contacts between the elements, or fabricating each active acoustic element such that signal and ground electrodes reside at different regions of the proximal surface of the active acoustic element and including a second electrically conductive pin that contacts the ground electrode and extends from the proximal surface.

While FIGS. 14A and 14B show slots 640 in the grid housing 600 for supporting and routing ground wires among the active acoustic elements 100, the ground wires are not shown in the figures.

Figure 14F:
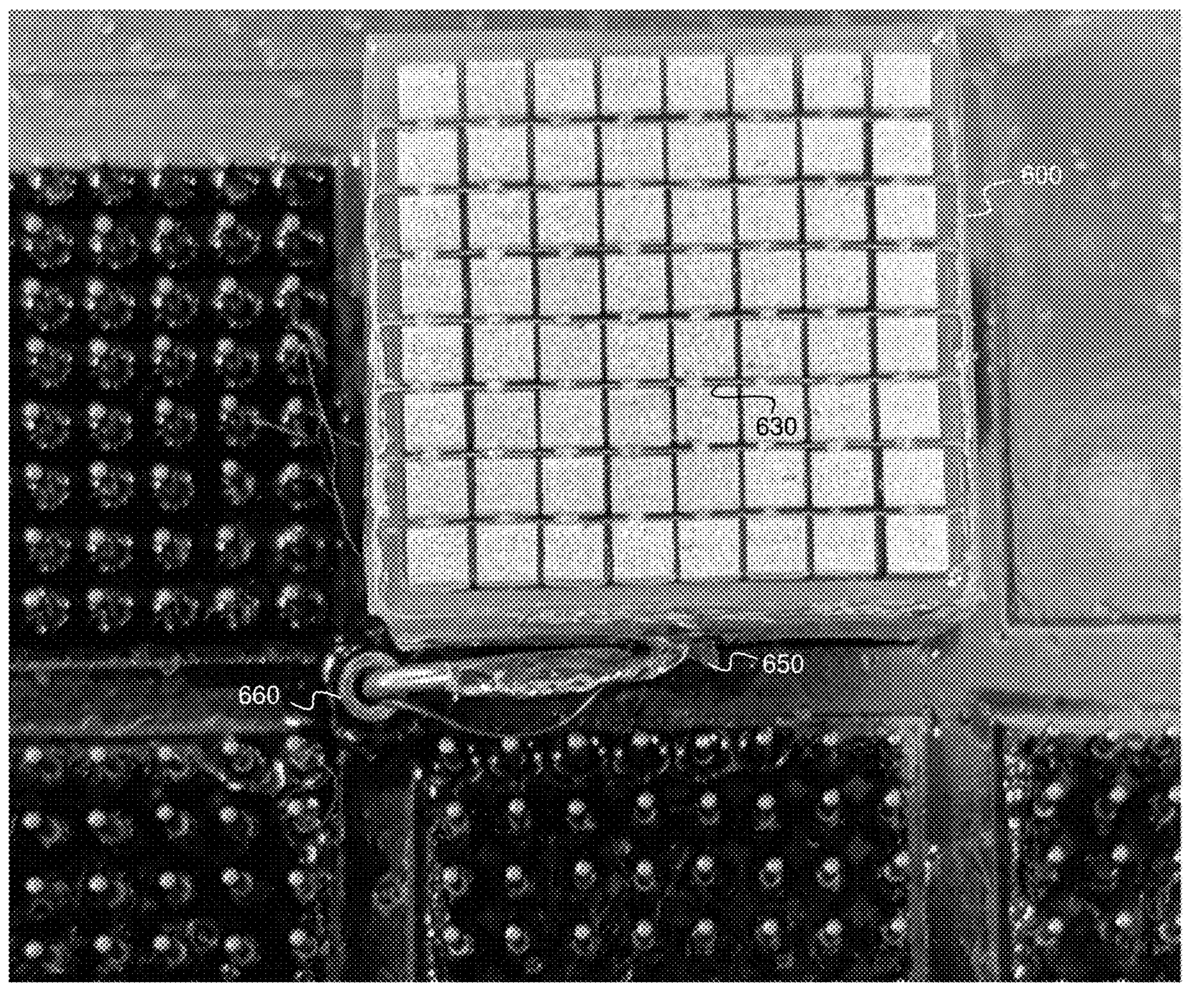

FIG. 14F is a photograph showing a top view of an example array module, illustrating the connection of ground wires and the routing of the ground wires in a proximal direction for passage through the heat exchanger. Wires 630 run horizontally between each row of the active acoustic elements 100. Each wire 630 is connected to the outer ground electrode of the active acoustic elements that are adjacent to the wire by a small amount of conductive epoxy (although alternative arrangements, such as spring connections, are possible, as noted). The wires 630 exit the grid housing 600 through slots 640 in the sides of the grid housing (these slots are visible, for example, in FIG. 14A). The wires 630 run along the edge of the grid (vertically, in the photo) and are bundled into a single wire grouping (bottom of module in photo, shown at 650). This ground wire bundle is soldered to the ground connection 660 that passes through the heat exchanger, as described in further detail below, and is electrically connected to the circuit board after passing through the heat exchanger. A thin membrane may be included across the water contact surface of the active acoustic elements 100 and grid frame 600. Such a membrane provides waterproofing and electrical isolation from the target medium.

The use of the grid frame 600 and the insert 610 may be beneficial in facilitating a bottom-up array fabrication approach. Through such an approach, each individual active acoustic element 100 has a location mechanically defined by the grid frame 600 and insert 610. During assembly, each active acoustic element 100 is inserted into its respective support location in the grid frame 600. While the present example embodiment employs a square lattice of active acoustic elements, other element sizes and shapes may be employed in a different grid geometry. For example, elements having a hollow cylindrical shape may be arranged in a hexagonal array.

In the present example embodiment, the first segments 131 of the electrically conductive members are metal pins. A given active acoustic element 100 may be mechanically and electrically secured its respective pin by a small application of conductive epoxy. As explained above, a pin is but one example of an electrically conductive member for contacting an active acoustic element. Other example implementations include, but are not limited to, a conductive foil (either introduced as part of the active acoustic element fabrication or added during array assembly), balls of low-temperature solder, anisotropic conducting epoxy, or a spring contact either aligned with the axis of the active acoustic element or pressing against the side of the active acoustic element.

The present example embodiment employs a configuration in which the majority of the active acoustic element is free from contact with a solid or liquid (e.g. air-backed). This configuration allows optimal ultrasound power transfer into the target medium. As explained above, depending on the requirements of the application, a backing material may alternatively be employed, for example, an epoxy backing for use in a diagnostic application.

As shown in FIGS. 11 and 12, the sockets 133 of the array module 300 may be directly contacted with distal ends of the cooling array of second segments of the electrically conductive members that contact the heat exchanger during modular assembly of the ultrasound array system. However, as shown in FIGS. 14D and 14E, in an alternative example, the sockets 133 may receive and pins of an intermediate connection board 670. As shown in the figures, the intermediate connection board 670 includes additional proximal sockets that can receive either the second segments of the electrically conductive members (the cooling pins) or pins of yet another intermediate connection board 670. The intermediate connection board 670 may be beneficial in facilitating modular assembly and varying the offset, in the proximal direction, of one component relative to another.

Figure 15:
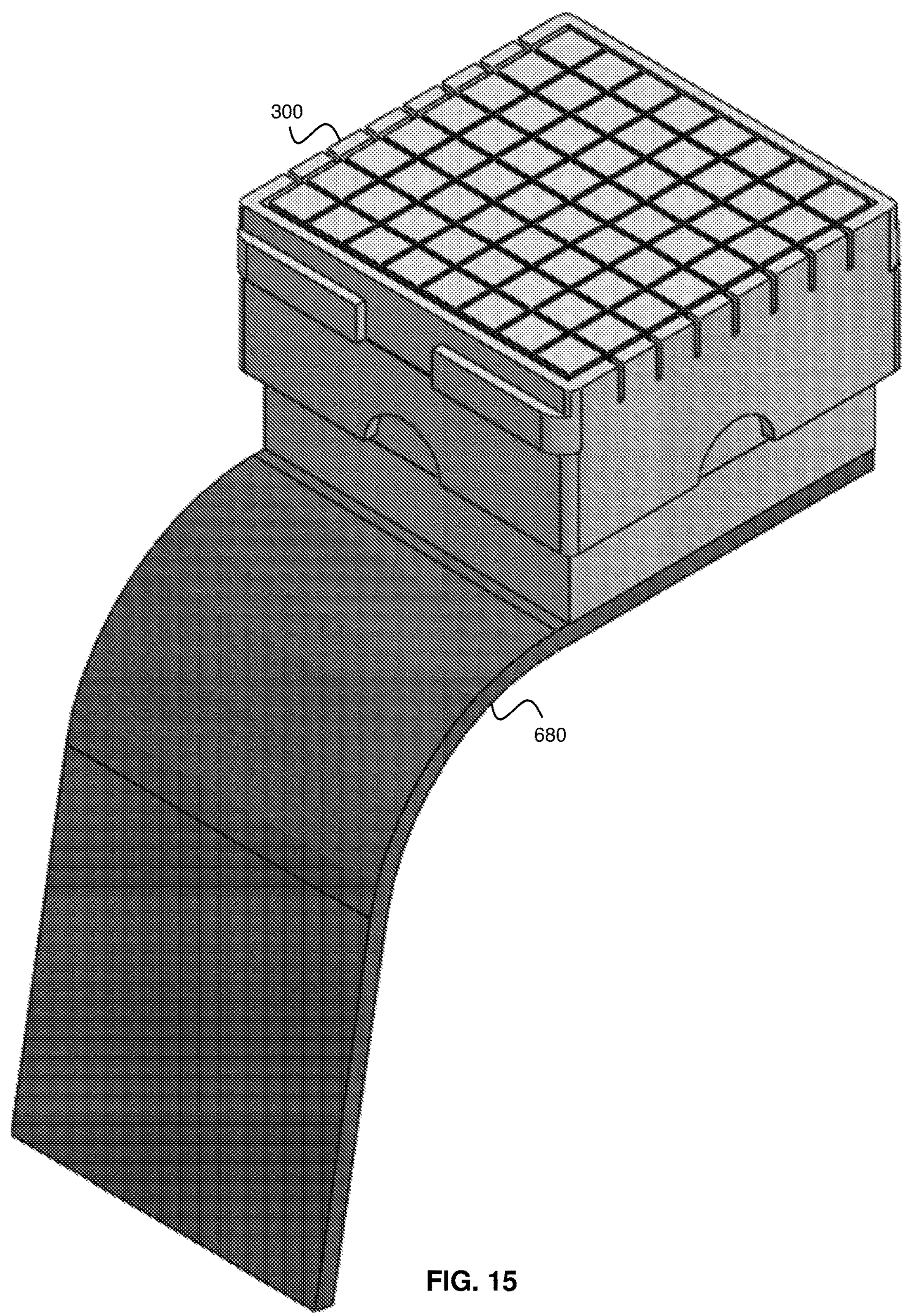
FIG. 15 shows an example array module connected to a printed circuit board for testing prior to assembly with a heat exchanger.

FIG. 15 demonstrates how the example array module 300 can be tested prior to assembly with the heat exchanger by electrically interfacing the array module 300 with a flexible printed circuit board 680 that can be connected to driving electronics. This may be achieved, for example, using a printed circuit board having an array of pins that can be received by the respective sockets of the array module.

As noted above, while a single array module may be interfaced with the second segments of the electrically conductive members that contact the heat exchanger (e.g. as shown in FIG. 11), in some example embodiments, two or more array modules may be combined into a larger ultrasound array, such that each array module contributes a sub-array of active acoustic elements to the larger ultrasound array. Such an example embodiment is illustrated in FIGS. 16, 17 and 18.

Figure 16:
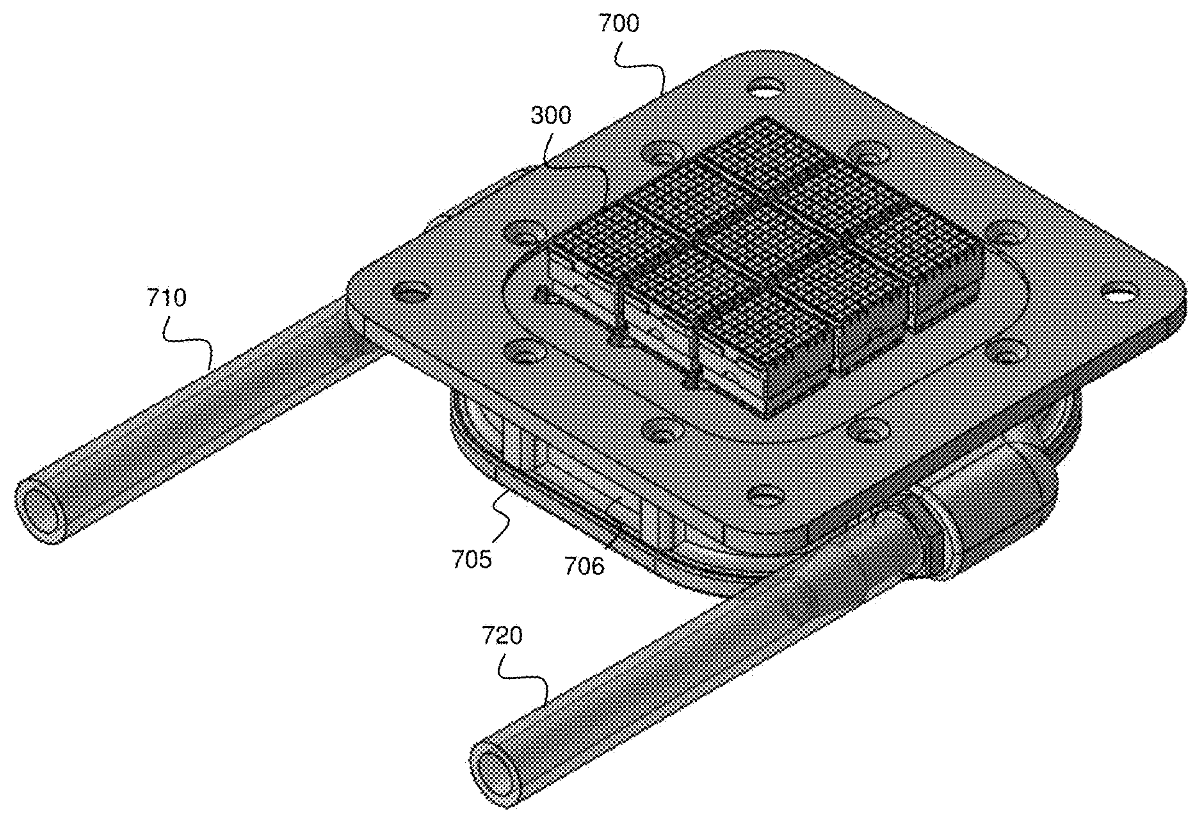
FIG. 16 shows an example multi-module ultrasound apparatus that includes a plurality of ultrasound array modules, where each ultrasound array module includes a dedicated array of proximally-extending electrically conductive members respectively contacting ultrasound array elements, and where each array of proximally-extending electrically conductive members extends to, and contacts, a common heat exchanger.

Referring first to FIG. 16, an example multi-module transducer array system is shown in which multiple array modules 300 are assembled to form a large ultrasound array. The example system includes a proximal heat exchanger having an inner chamber defined by a top plate 700, a bottom plate 705 and a side wall 706, with an inlet 710 and an outlet 720. An electrically insulating fluid is flowed through the heat exchanger. A set of array modules 300 are supported on the distal side of the heat exchanger. As per some of the preceding example embodiments, electrically conductive members extend from the proximal surfaces of the active acoustic elements of the array modules 300 and contact the heat exchanger to remove heat from the active acoustic elements.

Figure 17:
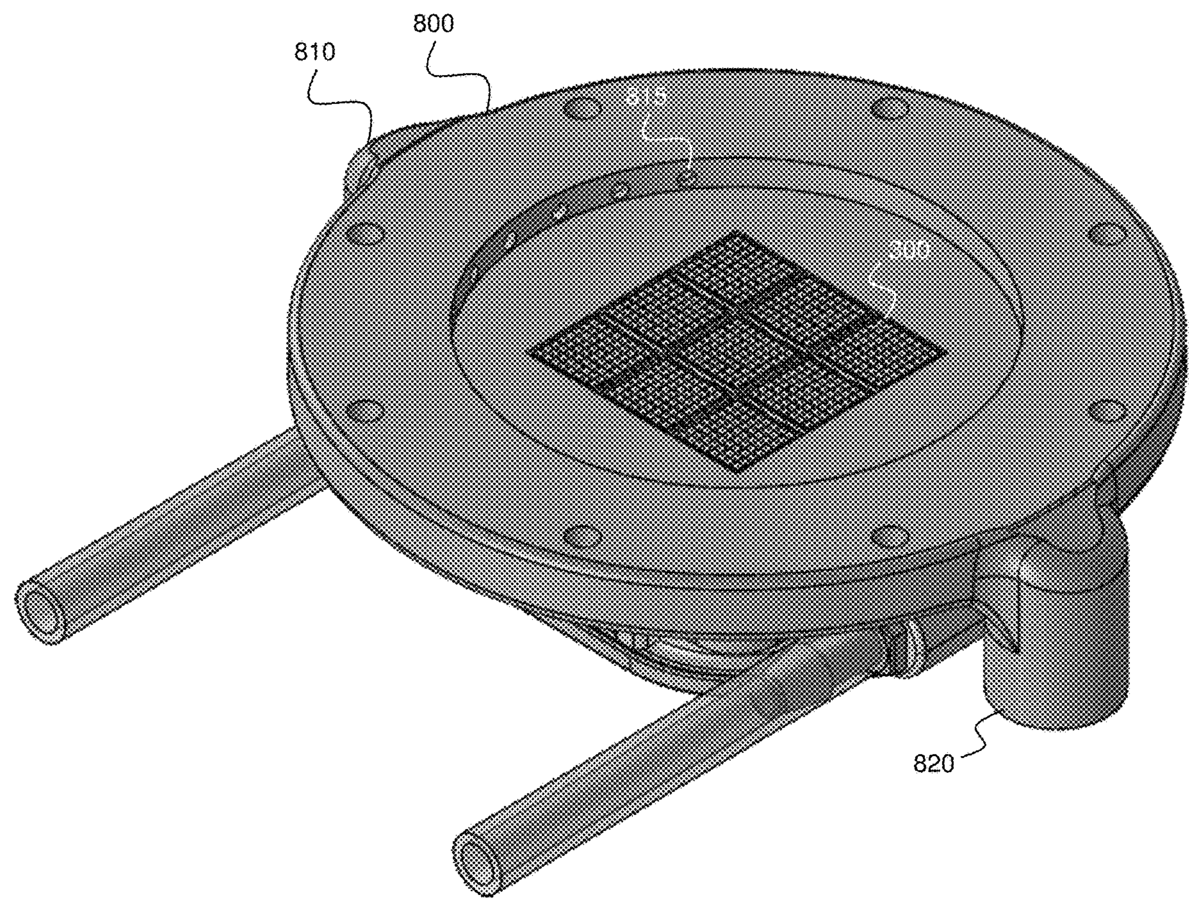
FIG. 17 shows the example multi-module ultrasound apparatus with a distal heat exchanger configured for cooling the distal side of each ultrasound array module.
Figure 18:
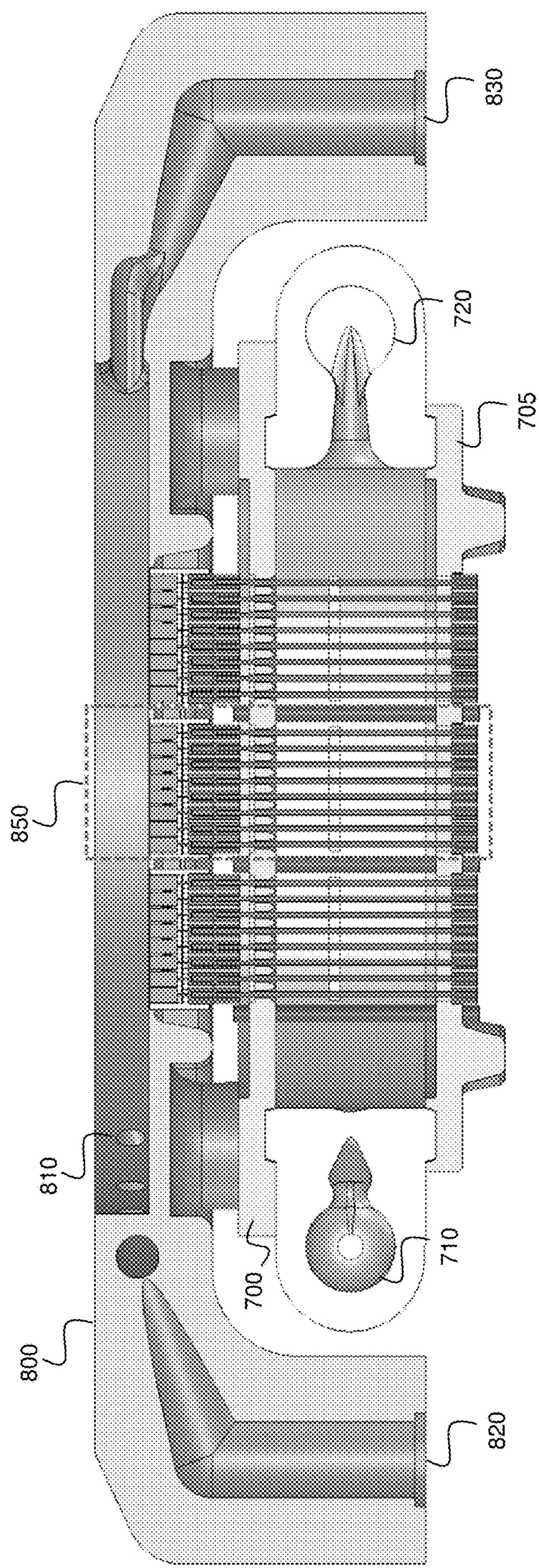
FIG. 18 shows a cross-section of the example multi-module ultrasound apparatus.

FIGS. 17 and 18 show the inclusion of an optional distal heat exchanger 800 which has an inlet port 810 and an outlet port 820. An additional cover plate (not shown) encloses the recessed region formed over the distal surfaces of the array modules 300 and cooling fluid enters the cavity through inlets 815 that are in fluid communication with the inlet port 810. The cooling fluid flows over the distal surfaces of the array modules 300 to provide distal-side cooling. The distal heat exchanger may circulate a volume of cold degassed water that provides coupling to the target tissue and cooling of the array elements.

Referring now to FIG. 18, a cross-sectional view of the ultrasound array system of FIG. 17 is shown. Three array modules are shown residing between the proximal and distal heat exchangers, with multi-segment pins (electrically conductive members) extending from the proximal surface of each active acoustic element, through the distal heat exchanger where they contact the electrically insulating fluid, and emerge on the proximal side of the proximal heat exchanger, where they are connectable to drive electronics (e.g. via connection to one or more connectors, cables or circuit boards).

Figure 19:
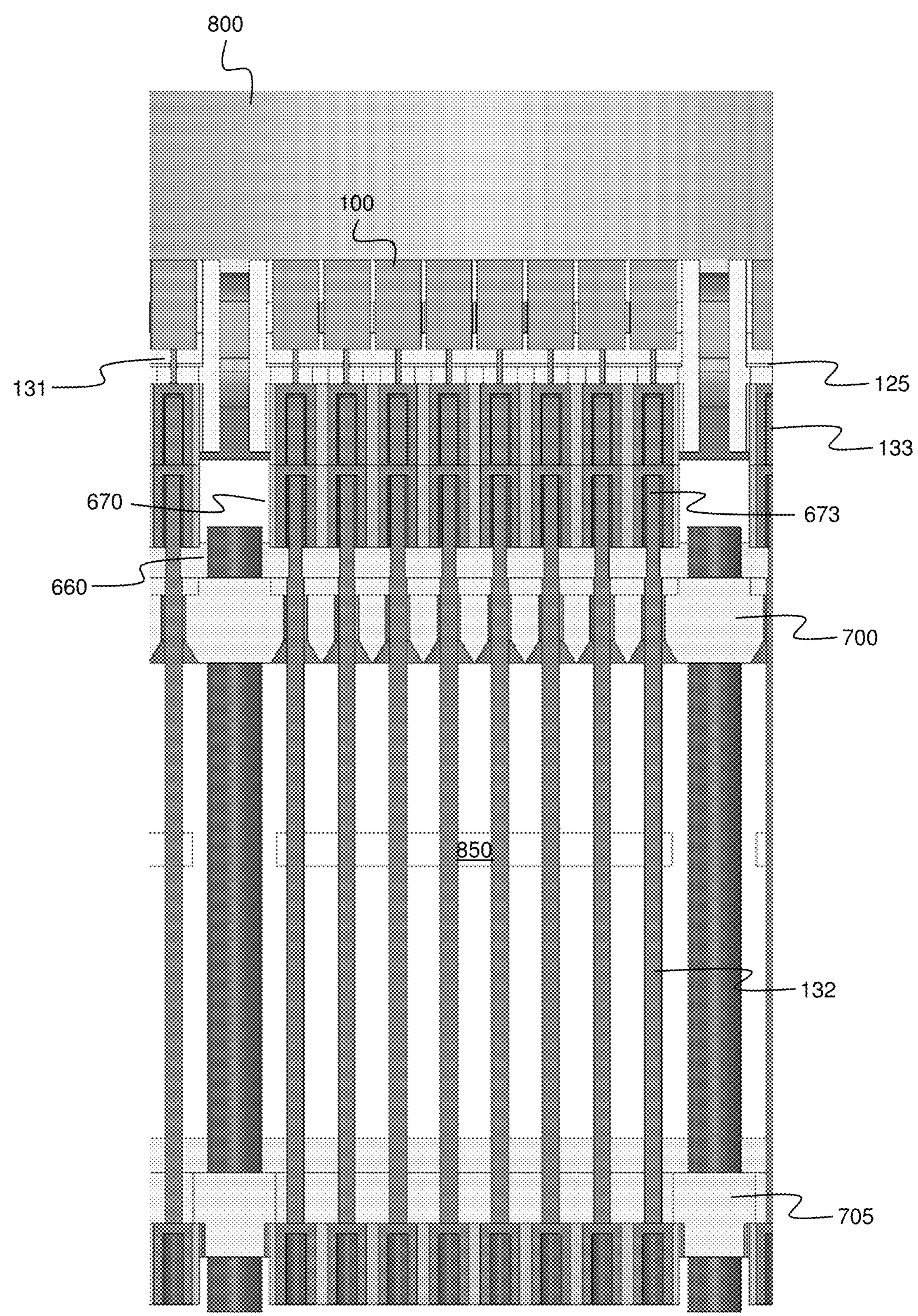
FIG. 19 shows a detailed cross-section sectional view of the example multi-module ultrasound apparatus.

FIG. 19 shows a detailed view of the region enclosed within a dashed rectangle 850 of FIG. 18, with a view that is centered on a single array module. The active acoustic elements 100 of the array module reside below the distal heat exchanger 800, with the grid frame of the array module establishing an air gap 125 on the proximal side of each active acoustic element, such that a first segment 131 of each electrically conductive member traverses the gap. The sockets 133 that are supported by the grid frame receive distal pins of the intermediate connection board 670, which provides additional sockets 673 that receive the second segments 132 of the electrically conductive members that pass through the heat exchanger (enclosed by distal and proximal plates 700 and 705) and contact the electrically insulating fluid. As shown in the figure, an intermediate electrically insulating spacer 850 may be provided to maintain spatial separation between the electrically conductive members within the internal region of the heat exchanger.

After passing through the heat exchanger, the second segments 132 of the electrically conductive members may be connected to the drive electronics through a cable or printed circuit board (such as a flexible printed circuit board). This ground wire bundle described above (but not shown in FIG. 19) is soldered to the ground connection 660 that passes through the heat exchanger. At the opposite side of the heat exchanger, the ground connection 660 is connected to a ground wire of the connector, cable or circuit board. Accordingly, once assembled into the final overall array, electrical connections may be made to the back side of each set of long pins. In alternative example embodiments involving an ultrasound array system assembled in the absence of a proximal heat exchanger, electrical connection can be made directly with the array module. In the present example embodiment, a flexible printed circuit board cable is attached to a mating connector that is connectable, on the proximal side of the heat exchanger, to each array module. This cable then runs to the driving electronics. Another example embodiment involves the mounting of the device on a PCB which either integrates the driving electronics or combines the connection of two or more array modules into a larger cable for connection to the electronics.

In the present example embodiment, epoxy was employed to seal the location at which each long pin passes through the proximal and distal plates of the heat exchanger. Alternative example embodiments may include the use of a circulating cooling gas or embedding the pins in a thermally conductive solid that is cooled by other means (e.g. fluid heat exchanger or an active cooling heat device such as a thermo-electric cooler).

The modular design of the present example embodiment greatly simplifies the assembly of several modules into a larger array, since the positioning of array modules and subsequent steps (such as waterproofing) can be performed without having to include cabling. Keeping the cable on a separate connector also reduces the fragility of the transducer module, since the module does not have the weight and torque of a cable. The cable may be included and supported after the full array assembly is complete.

In the present example embodiment, the locations of the array modules (and the active acoustic elements) are defined via the arrangement of the second segments of pins that are housed within the heat exchanger. In an alternative example embodiment, a lattice structure may be employed in which the array modules are assembled (e.g. via an adhesive or other attachment method) in place prior to electrical connection with the heat exchanger. In another example embodiment, the locations of the array modules may be defined by a rigid PCB.

The present inventors have found that the cold degassed water provided by the distal heat exchanger at the distal region of the ultrasound array assembly, combined with the proximal cooling provided by the proximal heat exchanger that contacts the active acoustic elements through the electrically conductive members, provides a cooling effect on both sides each transducer element, improving both the internal transducer temperature and the array cooling time. In the case of focused ultrasound therapeutic procedures, this design has been found to reduce overall focused ultrasound treatment times.

The present example system was implemented using electrically conductive members having a first segment with a diameter of 150 μm. This represents approximately 1% of the surface area of the element but is still thick enough to support the current required to drive the element at high power (e.g. approx. 70 mA in the example system that was implemented). The example system was found the achieve a maximum output power of approximately 170 mW per element of acoustic power, or ~11 W for a 64-element array module. This maximum power was found to be sustained for at least 30 to 60 seconds. Further testing demonstrated that the module was approximately 50% efficient, with the consequence that approximately 170 mW of heat per element was being generated.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An ultrasound apparatus comprising:

an active acoustic element configured to generate ultrasound energy when electrical drive signals are applied thereto, said active acoustic element having a distal surface for emitting the ultrasound energy in a distal direction and an opposing proximal surface;

an electrically conductive member contacting said active acoustic element for delivering electrical drive signals to said active acoustic element and for conducting heat from said active acoustic element, said electrically conductive member extending from said active acoustic element beyond said proximal surface such that at least a portion of said proximal surface of said active acoustic element is free from contact with said electrically conductive member, wherein said electrically conductive member is connectable to drive electronics for delivering the electrical drive signals to said active acoustic element through said electrically conductive member; and a heat exchanger spatially offset in a proximal direction from said proximal surface, said heat exchanger contacting a portion of said electrically conductive member residing beyond said proximal surface to remove heat from said active acoustic element through said electrically conductive member while delivering the electrical drive signals to said active acoustic element through said electrically conductive member;

wherein said heat exchanger comprises an electrically insulating fluid, said electrically insulating fluid contacting said portion of said electrically conductive member to remove the heat conducted through said electrically conductive member without contacting said active acoustic element.

2. The ultrasound apparatus according to claim 1 wherein a region of said proximal surface that is free from contact with said electrically conductive member is also absent from contact with a liquid or a solid, thereby facilitating reflection of ultrasound energy at said portion of said proximal surface.

3. The ultrasound apparatus according to claim 1 wherein a gap resides between said proximal surface and said heat exchanger, thereby facilitating reflection of ultrasound energy at said portion of said proximal surface, wherein said electrically conductive member extends across the gap to contact said heat exchanger.

4. The ultrasound apparatus according to claim 3 wherein the gap is an air gap.

5. The ultrasound apparatus according to claim 3 wherein the gap is filled with a gas other than air.

6. The ultrasound apparatus according to claim 1 wherein said proximal surface comprises a signal electrode, wherein a distal end of said electrically conductive member contacts said electrode.

7. The ultrasound apparatus according to claim 6 wherein a cross-sectional area of said electrically conductive member, within said portion of said electrically conductive member that contacts said heat exchanger, is greater than a cross-sectional area of said electrically conductive member at said distal end of said electrically conductive member.

8. The ultrasound apparatus according to claim 1 wherein a distal region of said electrically conductive member contacts an electrode of said active acoustic element.

9. The ultrasound apparatus according to claim 1 wherein said portion of said electrically conductive member contacting said electrically insulating fluid comprises a cylindrical segment.

10. The ultrasound apparatus according to claim 1 further comprising a pump configured to flow said electrically insulating fluid through said heat exchanger.

11. The ultrasound apparatus according to claim 1 wherein said heat exchanger is a first heat exchanger, said ultrasound apparatus further comprising a second heat exchanger located on a distal side of said distal surface, said second heat exchanger being in thermal communication with said active acoustic element, such that heat generated within said active acoustic element is removed on a proximal side of said active acoustic element by said first heat exchanger and is removed on a distal side of said active acoustic element by said second heat exchanger.

12. The ultrasound apparatus according to claim 1 further comprising a printed circuit board residing on a proximal side of said heat exchanger, wherein said electrically conductive member extends beyond said heat exchanger and is connected to said printed circuit board for delivering the electrical drive signals.

13. The ultrasound apparatus according to claim 1 wherein said electrically conductive member comprises a first segment contacting said active acoustic element and a second segment contacting said heat exchanger, wherein said first segment is detachably connected to said second segment to facilitate modular assembly of said ultrasound apparatus.

14. The ultrasound apparatus according to claim 13 wherein a cross-sectional diameter of said first segment is less than a cross-sectional diameter of said second segment.

15. The ultrasound apparatus according to claim 13 wherein one of said first segment and said second segment comprises a socket for receiving the other of said first segment and said second segment.

16. The ultrasound apparatus according to claim 13 further comprising a housing configured to support said active acoustic element and said first segment of said electrically conductive member.

17. The ultrasound apparatus according to claim 1 wherein said active acoustic element is a first active acoustic element and said electrically conductive member is a first electrically conductive member, said ultrasound apparatus further comprising one or more additional acoustic active elements, each additional acoustic active element having a respective additional electrically conductive member extending therefrom beyond a respective proximal surface thereof such that a portion of each additional electrically conductive member contacts said heat exchanger, said first active acoustic element and said additional acoustic active elements defining a set of active acoustic elements, and said first electrically conductive member and said additional electrically conductive member defining a set of electrically conductive members, wherein said set of active acoustic elements and said set of electrically conductive members are spatially arranged to form an ultrasound array.

18. The ultrasound apparatus according to claim 17 wherein said heat exchanger comprises an electrically insulating fluid, said electrically insulating fluid contacting said portion of each electrically conductive member to remove the heat conducted through said electrically conductive member.

19. The ultrasound apparatus according to claim 18 further comprising an insulating spacer residing within said heat exchanger, said insulating spacer configured to prevent contact between said electrically conductive members.

20. The ultrasound apparatus according to claim 17 further comprising a housing configured to support said set of active acoustic elements.

21. The ultrasound apparatus according to claim 20 wherein each electrically conductive member of said set of electrically conductive members comprises a first segment contacting a respective active acoustic element and a second segment contacting said heat exchanger, wherein each first segment is supported by said housing;

wherein said housing, said set of active acoustic elements and said set of first segments form an array module; and wherein said set of second segments form a cooling array supported by said heat exchanger; and wherein each first segment is detachably connected to a respective second segment, such that said array module is detachable from said cooling array to facilitate modular assembly of said ultrasound apparatus with said heat exchanger.

22. The ultrasound apparatus according to claim 21 wherein a cross-sectional diameter of said first segment is less than a cross-sectional diameter of said second segment.

23. The ultrasound apparatus according to claim 21 wherein one of said first segment and said second segment comprises a socket for receiving the other of said first segment and said second segment.

24. The ultrasound apparatus according to claim 21 wherein said array module is a first array module and said cooling array is a first cooling array, said ultrasound apparatus further comprising one or more additional array modules and one or more respective cooling arrays.

25. The ultrasound apparatus according to claim 24 wherein each array module is connected, through a respective cooling array, to a respective circuit board, and wherein each circuit board is connected to dedicated per-module drive electronics.

26. An ultrasound apparatus comprising:

an active acoustic element configured to generate ultrasound energy when electrical drive signals are applied thereto, said active acoustic element having a distal surface for emitting the ultrasound energy in a distal direction and an opposing proximal surface;

an electrically conductive member contacting said active acoustic element for delivering electrical drive signals to said active acoustic element and for conducting heat from said active acoustic element, said electrically conductive member extending from said active acoustic element beyond said proximal surface such that at least a portion of said proximal surface of said active acoustic element is free from contact with said electrically conductive member;

a circuit board spatially offset in a proximal direction from said proximal surface, wherein a proximal end of said electrically conductive member is in electrical contact with said circuit board for delivering the electrical drive signals to said active acoustic element; and a heat exchanger in thermal contact with said circuit board for removing heat conducted through said electrically conductive member and through said circuit board.

* * * * *